US012628841B2

(12) United States Patent
Sikes

(10) Patent No.: US 12,628,841 B2
(45) Date of Patent: May 19, 2026

(54) COMPOSITIONS, PROCESSES OF PRODUCTION, STERILIZATION, AND HEALTH-PROMOTING USES OF LYOPHILIZED MILK

(71) Applicant: AQUERO CANADA LTD., Calgary (CA)

(72) Inventor: C. Steven Sikes, Eugene, OR (US)

(73) Assignee: AQUERO CANADA LTD., Calgary (CA)

( * ) Notice: Subject to any disclaimer, the term of this patent is extended or adjusted under 35 U.S.C. 154(b) by 778 days.

(21) Appl. No.: 17/625,447

(22) PCT Filed: Jul. 9, 2020

(86) PCT No.: PCT/CA2020/050952
§ 371 (c)(1),
(2) Date: Jan. 7, 2022

(87) PCT Pub. No.: WO2021/003575
PCT Pub. Date: Jan. 14, 2021

(65) Prior Publication Data
US 2022/0256873 A1     Aug. 18, 2022

Related U.S. Application Data

(60) Provisional application No. 62/873,099, filed on Jul. 11, 2019, provisional application No. 62/872,056, filed on Jul. 9, 2019.

(51) Int. Cl.
| | |
|---|---|
| A23C 1/08 | (2006.01) |
| A23C 9/18 | (2006.01) |
| A23C 9/20 | (2006.01) |
| A61K 9/19 | (2006.01) |
| A61K 35/20 | (2006.01) |

(52) U.S. Cl.
CPC .................. *A23C 9/18* (2013.01); *A23C 1/08* (2013.01); *A23C 9/206* (2013.01); *A61K 9/19* (2013.01); *A61K 35/20* (2013.01)

(58) Field of Classification Search
None
See application file for complete search history.

(56) References Cited

U.S. PATENT DOCUMENTS

| | | | |
|---|---|---|---|
| 2,015,496 | A | 9/1935 | Platt |
| 3,297,455 | A | 1/1967 | Ogden |
| 4,376,072 | A | 3/1983 | Connolly |
| 4,519,945 | A | 5/1985 | Ottenhof |
| 6,472,003 | B2 | 10/2002 | Barrett-Reis |
| 7,659,111 | B2 | 2/2010 | Meir |
| 7,935,478 | B2 | 5/2011 | Natan |
| 8,147,894 | B2 | 4/2012 | Euber |
| 8,197,872 | B2 | 6/2012 | Mills |
| 8,287,931 | B2 | 10/2012 | Rosales |

| | | | |
|---|---|---|---|
| 8,361,511 | B2 | 1/2013 | Hill |
| 8,518,894 | B2 | 8/2013 | Friel |
| 8,545,920 | B2 | 10/2013 | Medo |
| 8,796,213 | B2 | 8/2014 | Underwood |
| 8,927,027 | B2 | 1/2015 | Fournell |
| 9,149,052 | B2 | 10/2015 | Medo |
| 9,439,448 | B2 | 9/2016 | Rosales |
| 9,457,058 | B2 | 10/2016 | Hondmann |
| 9,539,269 | B2 | 1/2017 | Chow |
| 9,574,169 | B2 | 2/2017 | Corveleyn |
| 9,609,888 | B2 | 4/2017 | Berg |
| 9,808,474 | B2 | 11/2017 | Buck |
| 9,808,475 | B2 | 11/2017 | German |
| 9,894,911 | B2 | 2/2018 | Odaka |
| 10,716,816 | B2 | 7/2020 | Kyle |
| 10,940,158 | B2 | 3/2021 | Sangild |

(Continued)

FOREIGN PATENT DOCUMENTS

| | | |
|---|---|---|
| CN | 101422240 A | 5/2009 |
| CN | 101530129 B | 9/2009 |

(Continued)

OTHER PUBLICATIONS

Dalli, J., N. Chiang, and C. N. Serhan. 2014. Identification of 14-series sulfido-conjugated mediators that promote resolution of infection and organ protection. Proceedings of the National Academy of Sciences 111, E4753-E4761.

Darragh, A,J, and P.J. Moughan, 1998. The amino acid composition of human milk corrected for amino acid digestibility. British Journal of Nutrition 80, 25-34.

Davies, D.P. 1997. Adequacy of expressed breast milk for early growth of preterm infants. Archives of Disease in Childhood 52, 296-301.

De Curtis, M., M. Canduso, C. Pieltain, and J. Rigo. 1999. Effect of fortification on the osmolality of human milk. Archives of Disease in Childhood. Fetal and Neonatal Edition 81, 141-43.

(Continued)

*Primary Examiner* — Jyoti Chawla
(74) *Attorney, Agent, or Firm* — MBM Intellectual Property Law LLP

(57) ABSTRACT

The present invention provides novel oral dosage comprising lyophilized mammalian (human) milk and optionally a physiologically acceptable excipient or carrier, and their use for improvement of mammalian (human) health. Also provided a novel process for preparing lyophilized mammalian milk with desired nutritional and cellular content, initially freezing raw milk obtained from a mammalian source, forming a layer of a predefined thickness from the frozen milk at a temperature from −4° C. to −80° C., and drying the formed layer at a temperature from −20° C. to +60° C. at a pressure from 5 micron Hg to atmospheric pressure to provide the lyophilized human milk. The process optionally comprises comprising treating said lyophilized milk via flash supercritical $CO_2$ treatment comprising soaking said lyophilized milk with supercritical $CO_2$

26 Claims, No Drawings

(56) References Cited

U.S. PATENT DOCUMENTS

| | | | |
|---|---|---|---|
| 11,020,413 | B2 | 6/2021 | Sangild |
| 2004/0040448 | A1 | 3/2004 | Dunker |
| 2009/0017176 | A1 | 1/2009 | Sugawara |
| 2010/0197017 | A1 | 8/2010 | Natan |
| 2011/0200610 | A1 | 8/2011 | Ilan |
| 2011/0305764 | A1 | 12/2011 | Kuklinski |
| 2017/0231262 | A1 | 8/2017 | Banavara |
| 2018/0064739 | A1 | 3/2018 | Chichlowski |
| 2018/0092374 | A1 | 4/2018 | Fournell |
| 2018/0103675 | A1 | 4/2018 | Chichlowski |

FOREIGN PATENT DOCUMENTS

| | | | |
|---|---|---|---|
| CN | 102429031 | B | 5/2012 |
| EP | 0064509 | A1 | 11/1982 |
| EP | 0424414 | A1 | 5/1991 |
| EP | 0450141 | A1 | 10/1991 |
| EP | 0450141 | B1 | 10/1991 |
| EP | 1168929 | B1 | 1/2002 |
| EP | 3791726 | A1 | 3/2021 |
| JP | 2016220674 | A | 12/2016 |
| JP | 2016220674 | A1 | 12/2016 |
| KR | 20090122071 | A | 11/2009 |
| KR | 20190032870 | A * | 3/2019 |
| WO | 00/60949 | A2 | 10/2000 |
| WO | 2006026878 | A1 | 3/2006 |
| WO | 2006041316 | A1 | 4/2006 |
| WO | 2012030764 | A2 | 3/2012 |
| WO | 2013011040 | A1 | 1/2013 |
| WO | 2020168439 | A1 | 8/2020 |
| WO | 2021/003575 | A1 | 1/2021 |

OTHER PUBLICATIONS

Dela Pena, I.J.I., E. Hong, J.B. de la Peña, H.J. Kim, C.J. Botanas, Y.S. Hong, Y.S. Hwang, B.S. Moon, and J.H. Cheong 2015. Milk collected at night induces sedative and anxiolytic-like effects and augments pentobarbital-Induced sleeping behavior in mice. Journal of Medicinal Food 18, 1255-61, 2 page article "Medicating elderly with night milk" by Petherick.

De Souza Grance, T.R., P. de Oliveira Serafin, D.M.C. Thomaz, and D.B. Palhares. 2015. Homologous human milk supplement for very low birth weight preterm infant feeding. Revista Paulista de Pediatria 33, 28-33.

Denizil, A. 2011. Plasma fractionation: conventional and chromatographic methods for albumin purification. Hacettepe Journal of Biology and Chemistry 39, 315-341.

Dionisi, F., et al.: "Supercritical CO2 Extraction for Total Fat Analysis of Food Products", Journal of Food Science, vol. 64, No. 4, 1999, pp. 612-615.

Ebaid, H., B. Abdel-Salam, I. Hassan, A. Al-Tamimi, A. Metwalli, and I. Alhazza. 2015. Camel milk peptide improves wound healing in diabetic rats by orchestrating the redox status and immune response. Lipids in Health and Disease. 14, 132-41.

Eidelman, A.I. and R.J. Schanler. Breastfeeding and the use of human milk. Pediatrics 129, e827-e841, 2017 version 23 pages.

El-Shafei, M.M., N.S. Al-Amoudy, and A.K. Said. 1988 a. Effect of the drying process on the nutritive value of milk. Part 1. Biochemical composition. Die Nahrung Molecular Journal of Nutrition 32, 553-57, Abstract only 1 page.

El-Shafei, M.M., N.S. Al-Amoudy, and A.K. Said. 1988 b. Effect of the drying process on the nutritive value of milk. Part 2. Biological evaluation. Die Nahrung Molecular Journal of Nutrition 32, 559-64, Abstract only.

Erkman, O. 1997. Antimicrobial effect of pressurized CO2 on *Staphylococcus aureus* in broth and milk. Journal of Food Science and Technology 71, 826-829, Abstract only.

Fatemeh, S., S. Mustafa, A. Ariff, and Y.A. Manap. 2011. Optimization of a cryoprotective medium and survival of freeze-dried Bifidobacterium infantis 20088 throughout storage, rehydration and gastrointestinal tract transit for infant formula probiotic applications. African Journal of Microbiology Research 5, 3373-84.

Fichter, M., M. Klotz, D.L. Hirschberg, B. Waldura, O. Schofer, S. Ehnert, L.K. Schwarz, C.V. Ginneken, and K.H. Schäfer. 2011. Breast milk contains relevant neurotrophic factors and cytokines for enteric nervous system development. Molecular Nutrition and Food Research 55, 1592-6.

Friend, B.A., K.M. Shahani, C.A. Long, and L.A. Vaughn, 1983, Evaluation of freeze-drying, pasteurization, high-temperature heating and storage on selected enzymes, B-vitamins, and lipids of mature human milk. Journal of Food Protection 46, 330-334.

Friend, B.A., K.M. Shahani,, C.A. Long, and L.A. Vaughn. 1983b. The effect of processing and storage on key enzymes, B vitamins, and lipids of mature human milk I. Evaluation of fresh samples and effects of freezing and frozen storage. Pediatric Research 17, 61-64.

Food and Drug Administration. 2013. Ion exchange resins. Code of Federal Registration CFR 21, 173.25, 124-128.

Food and Drug Administration. 2018. Infant formula: the addition of minimum and maximum levers of Selenium to infant formula and related labeling requirements. Code of Federal Registration CFR 80, 35834-35841.

Fusch, G., N. Rochow, A. Choi, S. Fusch, S. Poeschl, A. O. Ubah, S-Y Lee, P. Raja, and C. Fusch. 2015. Rapid measurement of macronutrients in breast milk: How reliable are infrared milk analyzers. Clinical Nutrition 34, 465-76.

Garofalo, R. 2010. Cytokines in human milk. The Journal of Pediatrics 156, Suppl. 1, 36-40.

Goldman, A.S. 1993. The immune system of human milk: antimicrobial, antiinflammatory and immunomodulating properties. The Pediatric Infectious Disease Journal 12, 664-71, Abstract only.

Gomez-Gallego, C., M.C. Collado, G. Perez, T. Ilo, U.M. Jaakkola, M.J. Bernal, M. J. Periago, R. Frias, G. Ros, and S. Salminen. 2013. Resembling breast milk: influence of polyamine-supplemented formula on neonatal BALB/cOlaHsd mouse microbiota. British Journal of Nutrition 111, 1050-58, Abstract only.

Gopinath, B., V.M. Flood, J.C. Louie, J.J. Wang, G. Burlutsky, E. Rochtchina, and P. Mitchell. 2014. Consumption of dairy products and the 15-year incidence of related macular degeneration. British Journal of Nutrition 111, 1673-79, Abstract only.

Gozen, D., S. Caglar, S. Bayraktar, and F. Atici. 2014. Diaper dermatitis care of newborns human breast milk or barrier cream. Journal of Clinical Nursing 23, 515-23, Abstract only.

Greaves, R.I.N. 1960. Preservation of living cells by freeze-drying. Annals of the New York Academy of Sciences 13, 723-8, Abstract/ excerpt only.

Gurnida, D.A., A.M. Rowan, P. Idjradinata, D. Muchtadi, and N. Sekarwana. 2012. Association of complex lipids containing gangliosides with cognitive development of 6-month-old infants. Early Human Development 88, 595-601, Abstract/ excerpt only.

Gutierrez, D. and J.A.G. de Almeida. 1998. Currents in human milk banking: human milk banks in Brazil. Journal of Human Lactation 14, 333-5, Abstract/ excerpt only.

Hahn-Holbrook, T.B. Le, A. Chung, E.P. Davis, and L.M. Glynn. 2016. Cortisol in human milk predicts child BMI (body mass index). Obesity 24, 2471-2474, Abstract/ excerpt only.

Hartel, R.W. 2001. Crystallization in Foods. Springer. 325 pgs, preface of book only only.

Hassiotou, F., A. Beltran, E. Chetwynd, A.M. Stuebe, A-J Twigger, P. Metzger, N. Trengove, C.T. Lai, L. Filgueira, P. Blancafort, and P.E. Hartmann. 2012. Breastmilk Is a Novel Source of Stem Cells with Multilineage Differentiation Potential. Stem Cells 2012, 2164-2174.

Hassiotou, F., D.T. Geddes, and P.E. Hartmann. 2013. Cells in human milk: state of the science. Journal of Human Lactation 29, 171-82, Abstract/ excerpt only.

Hassiotou, F., A. Mobley, D. Geddes, P. Hartmann, and T. Wilkie. 2015. Breastmilk imparts mother's stem cells to the infant. FASEB Journal 29, 876, 4 page excerpt only.

Hempsey, W. 2015. They don't call it liquid gold for nothing. Myrtle Beach Birth Services.

Hofland, G.W., M van Es, L.A.M van der Wielen, and G-J Witkamp. 1999. Isoelectric precipitation of casein using high-pressure CO2. Industrial and Engineering Chemistry Research 38, 4919-27.

(56)          References Cited

OTHER PUBLICATIONS

Hofland, G.W., M. Berkhoff, G.J. Witkamp, and L.A.M. van der Wielen. 2003. Dynamics of precipitation of casein with carbon dioxide. International Dairy Journal 13, 685-97.

Honour, P. and J.M. Dolby. 1979. Bacteriostasis of *Escherichia coli* by milk. III. The activity and stability of early, transitional and mature human milk collected locally. Journal of Hygiene 83, 243-54.

Hossain, Z., W. Diehl-Jones, D.S. Mackay, A. Chui, and J.K. Friel. 2014. Human milk and the premature infant. In, Handbook of dietary and nutritional aspects of bottle feeding, chapter 18, Wageningen Academic, Eds. V.R. Preedy, R.R. Watson, and S. Zibadi. 34 p.

Hubalek, Z. 2003. Protectants used in the cryopreservation of microorganisms. Cryobiology 46, 205-229.

Hylmo, P., S. Polberger, I. Axelsson, I. Jakobsson, and N. Raiha. 1984. Preparation of fat and protein from banked human milk: its use in feeding very-low-birth-weight infants. In, Human Milk Banking, A.F. Williams and J.D. Baum, eds. Vevey/Raven Press. pp. 55-56, pp. 55-61.

Idrus, N.F.M., L.N. Yian, Z. Idham, N.A. Aris, N.R. Putra, A.H.A. Aziz, and M.A.C. Yunus. 2018. Mini review: application of supercritical carbon dioxide in extraction of propolis extract. Malaysian Journal of Fundamental and Applied Sciences 14, 387-396.

Iskarpatyoti, J., E.A. Morse, R.P. McClung, M. Ikizler, J.D. Wetzel, N. Contractor, and T.S. Dermody. 2012. Serotype specific differences in inhibition of reovirus infectivity by human-milk glycans are determined by viral attachment protein. Virology 433, 489-97, Abstract only.

Iwamori, M., K. Takamizawa, M. Momoeda, Y. Iwamori, and Y Taketani. 2008. Gangliosides in human, cow and goat milk, and their abilities as to neutralization of cholera toxin and botulinum type A neurotoxin. Glycoconjugate Journal 25, 675-83, Abstract only.

Jablonka, M.S. and P.A. Munro. 1985. Particle size distribution and calcium content of batch-precipitated acid casein curd: effect of precipitation temperature and pH. Journal of Dairy Research 52, 419-28.

Office Action dated Feb. 22, 2024 (Corresponding Canadian Application No. 3,146,184).

Office Action dated Mar. 5, 2024 (Corresponding Canadian Application No. 3,130,834).

Janjindamai, W. and T. Chotsampancharoen. 2006. Effect of fortification on the osmolality of human milk. Journal of the Medical Association of Thailand 89, 1400-03.

Jarvinen, K.M. and H. Suomalainen. 2002. Leucocytes in human milk and lymphocyte subsets in cow's milk-allergic infants. Pediatric Allergy and Immunology 13, 243-54, Abstract only.

Jiang, R. and B. Lonnerdal. 2016. Biological roles of milk osteopontin. Current Opinion in Clinical Nutrition and Metabolic Care 19, 214-9, Abstract only.

Jones, F. 2003. History of North American donor milk banking: one hundred years of progress. Journal of Human Lactation 19, 313-18.

Tomasula, P. et al. Preparation of Casein Using Carbon Dioxide. 1995. J Diary Sci. 78:506-514.

Keim, S.A., U.S. Hogan, K.A. McNamara, V. Gudimetla, C.E. Dillon, J.J. Kwiek, and S.R. Geraghty. 2013. Microbial contamination of human milk purchased via the internet. Pediatrics 132, e1227-e1235.

Khailova, L., K. Dvorak, K.M. Arganbright, C.S. Williams, M.D. Halpern, and B. Dvorak. 2009. Changes in hepatic cell junctions structure during experimental necrotizing enterocolitis: effect of EGF treatment. Pediatric Research 66, 140-4, Abstract only.

Kitano, N., K. Tsunoda, T. Tsuji, Y. Osuka, T. Jindo, K. Tanaka, and T. Okura. 2014. Association between difficulty initiating sleep in older adults and the combination of leisure-time physical activity and consumption of milk and milk products: a cross-sectional study. Biomed Central (BMC) Geriatrics 14, 118-25, Abstract only.

Knight, C.A., C.C. Cheng, and A.L. DeVries. 1991. Adsorption of a-helical antifreeze peptides on specific ice crystal surface planes. Biophysical Journal 59, 409-418.

Koch, L.E. 2002-2017. Discover the power of horsemilk. www. powerofhorsemilk.com (Netherlands), Abstract only.

Koettnitz, F. 2018. Freeze-drying of breast-milk. Elacta European Lactation Consultants Alliance, Feb. 2018, p. 1-4.

Koo, W. and H. Tice. 2018. Human milk fortifiers do not meet the current recommendation for nutrients in very low birth weight infants. Journal of Parenteral and Enteral Nutrition 42, 813-820, Abstract only.

Kumaran, R.S. 2015-2018, Miracle Tree Life Science, www. miracletree.in, 17 pages document.

Kunz, C., S. Rudloff, W. Baier, N. Klein, and S. Strobel. 2000. Oligosaccharides in human milk: structural, functional, and metabolic aspects. Annual Review of Nutrition 20, 699-722, Abstract only.

Lamireau, D. 2015. Lyophilization in the human milk of Marmande. Third international congress of the European milk bank association.

Larque, E., M. Sabater-Molina, and S. Zamora. 2007. Biological significance of dietary polyamines. Nutrition 23, 87-95, Abstract only.

Li, C., N.W. Solomons, M.E. Scott, and K.G. Koski. 2016. Minerals and trace elements in human breast milk are associated with Guatamalan infant anthropometric outcomes within the first 6 months. Journal of Nutrition 146, 2067-74.

Lin A.E., C.A. Autran, S.D. Española, L. Bode, and V. Nizet. 2014. Human milk oligosaccharides protect bladder epithelial cells against uropathogenic *Escherichia coli* invasion and cytotoxicity. The Journal of Infectious Diseases 209, 389-98, Abstract only.

Lin A.E., C.A. Autran, A. Szyszka, T. Escajadillo, M. Huang, K. Godula, A.R. Prudden, G. Boons, A.L. Lewis, K.S. Doran, V. Nizet, and L. Bode. 2017. Human milk oligosaccharides inhibit growth of group B *Streptococcus*. Journal of Biological Chemistry 292, 11243-49, Abstract only.

Linhardt, R. and H.G. Bazin. 2001. Separation and purification of carbohydrates. In: Fraser-Reid B.O., Tatsuta K., Thiem J. (eds.) Glycoscience: Chemistry and Chemical Biology I-III. Springer, Berlin, Heidelberg. Chapter 1.3, p. 63-74.

Liu, B. and D.S. Newburg. 2013. Human milk glycoproteins protect infants against human pathogens. Breastfeeding Medicine 8, 354-62.

Loser, C. 2000. Polyamines in human and animal milk. British Journal of Nutrition 84, 55-58.

Lozano, B., A.I. Castellote, R. Montes, and M.C. Lopez-Sabater. 2014. Vitamins, fatty acids, and antioxidant capacity stability during storage of freeze-dried human milk. International Journal of Food Science and Nutrition 65, 703-7, Abstract only.

Lucas, A., P.J. Lucas, S.I. Chavin, R.L. Lyster, and J.D. Baum. 1980. A human milk formula. Early Human Development 4, 15-21, Abstract only.

Machado, B.A.S., R.P.D. Silva, G. de Abreu Barreto, S.S. Costa, D.F. da Silva, H.N. Brandao, J.L.C. da Rocha, O.A. Dellagostin, J.A.P. Henriques, M.A. Umsza-Guez, and F.F. Padilha. 2016. Chemical composition and biological activity of extracts obtained by supercritical extraction and ethanolic extraction of brown, green and red propolis derived from different geographic regions in Brazil. PLOS One, p. 1-26.

Mahore, J.G., K.J. Wadher, M.J. Umekar, and P.K. Bhoyar. 2010. Ion exchange resins: pharmaceutical applications and recent advancement. International Journal of Pharmaceutical Sciences Review and Research 1, 8-13.

Malgorzata Witkowska-Zimny et al: "Milk Therapy; Unexpected Uses for Human Breast Milk", Nutrients, vol. 11, No. 5, p. 944, Apr. 26, 2019, 12 page document.

Malik, K.A. 1988. A new freeze-drying method for the preservation of nitrogen-fixing and other fragile bacteria. Journal of Microbiological Methods 8, 259-71.

Martin, C.R., P. Ling, and G.L. Blackburn. 2016. Review of infant feeding: key features of breast milk and infant formula. Nutrients 8, 279-89.

Martin, J.A., Hamilton, B.E., Osterman, M.J.K., and A.K. Driscoll. 2019. Births: Final Data for 2018, National Vital Statistics Reports, 47 pages.

(56) References Cited

OTHER PUBLICATIONS

McHugh, M. and V. Krukonis. 2013. Supercritical fluid extraction: Principles and practice. 2nd edition. Butterworth-Heinemann. 608 p, book cover only.

McJarrow, P., N. Schnell, J. Jumpsen, and T. Clandinin. 2009. Influence of dietary gangliosides on neonatal brain development. Nutrition Reviews 67, 451-63, Abstract only.

Mehra, R., P. Marnila, and H. Korhonen. 2006. Milk immunoglobulins for health promotion. International Dairy Journal 16, 1262-71.

Mercer, D. 2018. Ice crystal formation. The World of Food Science, 101. 3 pgs.

Minami, J., T. Odamaki, N. Hashikura, F. Abe, and J.Z. Xiao. 2016. Lysozyme in breast milk is a selection factor for bifidobacterial colonisation in the infant intestine. Beneficial Microbes 7, 53-60, Abstract only.

Miyamoto-Shinohara, Y., J. Sukenobe, T. Imaizumi, and T. Nakahara. 2008. Survival of freeze-dried bacteria. Journal of General and Applied Microbiology 54, 9-12.

Mizuno, K. 2019. Human milk bank and donor milk in Japan. International Society for Research in Human Milk and Lactation, First ISRHML China Workshop, Beijing. Abstract.

Moro, G.E., C. Billeaud, B. Rachel, J. Calvo, L. Cavallarin, L. Christen, D. Escuder-Vieco, A. Gaya, D. Lembo, A. Wesolowska, S. Arslanoglu, D. Barnett, E. Bertino, C-Y Boquein, C. Gebauer, A. Grovslien, G.A. Weaver, and J-C. Picaud. 2019. Processing of donor human milk: update and recommendations from the European Milk Bank Association (EMBA). Frontiers in Pediatrics 7, article 49, 1-10.

Morrow, A.L., G.M. Ruiz-Palacios, M. Altaye, X. Jiang, M.L. Guerrero, J.K. Meinzen-Derr, T. Farkas, P. Chaturvedi, L. K. Pickering, and D.S. Newburg. 2004. Human milk oligosaccharides are associated with protection against diarrhea in breast-fed infants. Journal of Pediatrics 145, 297-303, Abstract only.

Nagashima, K., K. Itoh, and T. Kuroume. 1990. Levels of insulin-like growth factor I in full- and preterm human milk in comparison to levels in cow's milk and in milk formulas. Biology of the Neonate 58, 343-6.

Nakamura, E., H. Uneyama and K. Torii. 2013. Gastrointestinal nutrient chemosensing and the gut-brain axis: Significance of glutamate signaling for normal digestion. Journal of Gastroenterology and Hepatology 28 (Suppl. 4): 2-8.

Newburg, D.S. 2013. Glycobiology of human milk. Biochemistry 78, 771-85, Abstract only.

Newburg, D.S., G.M. Ruiz-Palacios, M. Altaye, P. Chaturvedi, J. Meinzen-Derr, Mde L. Guerrero, and A.L. Morrow. 2004. Innate protection conferred by fucosylated oligosaccharides of human milk against diarrhea in breastfed infants. Glycobiology. 14, 253-63.

Newmark, L.M. 2017. Milk's bioactive ingredients help wounds heal faster. Splash! Milk Science Update, Feb. 2017, Multiple copies of the article abstract.

Northrop, J.H. 1923. Note on the purification and precipitation of casein. Journal of General Physiology 5, 749-50.

O'Connor, C.J., J.R. Longbottom, and P. Walde. 1986. Inactivation of bile-salt-stimulated human milk esterase: effect of storage and heat. Journal of Pediatric Gastroenterology and Nutrition 5, 630-637.

Oftedal, O.T. 2013. Origin and evolution of the major constituents of milk. In: McSweeney P., Fox P. (eds.), Advanced Dairy Chemistry. Springer, Boston, MA. p. 1-42, Abstract only.

Oliveira, D.L., A. Wilbey, A.S. Grandison, and L.B. Roseiro. 2015. Milk oligosaccharides: a review. International Journal of Dairy Technology 68, 305-21.

Yu, Z.T., N.N. Nanthakumar, D.S. Newburg. 2016. The Human Milk Oligosaccharide 2'-Fucosyllactose quenches Campylobacter jejuni-induced inflammation in human epithelial cells HEp-2 and HT-29 and in mouse intestinal mucosa. Journal of Nutrition 146, 1880-90, p. 1980 to 1990.

Yuen, B.H. 1988. Prolactin in human milk: The influence of nursing and the duration of postpartum lactation. American Journal of Obstetrics and Gynecology 158, 583-6, Abstract only.

Simmer, K. The Knowns and Unknowns of Human Milk Banking. 2011. Abstract.

Tomasula, P. et al. A continuous process for casein production using high-pressure carbon dioxide. Journal of Food Engineering. vol. 33, 1997, Abstract.

US Office Action dated Aug. 22, 2023, for U.S. Appl. No. 17/434,775 (Publication No. 2022/0000132), 11 pages.

Singh et al., Applications of Super Critical Fluid Extraction in Milk and Dairy Industry; A Review, J Food Process Technol 2018, 9:12, pp. 9 including cover sheet.

Buyukbese et al., Supercritical Carbon Dioxide Fractionation of Anhydrous Milk Fat, J Am Oil Chem Soc (2014) 91: 169-177.

Mohamed et al., The Use of Supercritical Fluid Extraction Technology in Food Processing, Food Technology Magazine, Jun. 2002, 15 page document.

Oliveira, Mariana M. et al.: "Development of human milk concentrate with human milk lyophilizate for feeding very low birth weight preterm infants: A preclinical experimental study", Department of Pediatrics, Children's Hospital, Riberiao Preto Medical School, University of Sao Paulo, Brazil, pp. 1-16, Feb. 20, 2019.

Pariente, B., S. Hu, D. Bettenworth, S. Speca, P. Desreumaux, M-A. Meuwis, S. Danese, F. Rieder, and E. Louis. 2019. Treatments for Crohn's disease-associated bowel damage: a systematic review. Clinical Gastroenterology and Hepatology 17, 847-856.

Patki, S., S. Kadam, V. Chandra, and R. Bhonde. 2010. Human breast milk is a rich source of multipotent mesenchymal stem cells. Human Cell 23, 35-40, Abstract only.

Patki, S., U. Patki, R. Patil, S. Indumathi, P. Kaingade, A. Bulbule, A. Nikam, and A. Pishte. 2012. Comparison of the levels of the growth factors in umbilical cord serum and human milk and its clinical significance. Cytokine 59, 305-8, Abstract only.

Pearson, F., M.J. Johnson, A.A. Leaf. 2013. Milk osmolality: does it matter? Archives of disease in childhood—Fetal and neonatal edition, 98, 166-69, Abstract only.

Peel, E., Y. Cheng, J.T. Djordjevic, S. Fox, T.C. Sorrell, and K. Belov. 2016. Cathelicidins in the Tasmanian devil (Sarcophilus harrisii). Nature, Scientific Reports 6, 1-9.

Perrin, M.T., J. Festival, J., S. Starks, L. Mondeaux, E.A. Brownell, and A. Vickers. 2019. Accuracy and reliability of infrared analyzers for measuring human milk macronutrients in a milk bank setting. Current Developments in Nutrition 3, 7 pgs, Abstract only.

Potocki, S. 2016. Potential health benefits of sphingolipids in milk and dairy products. Mljekarstvo (Dairy) 66, 251-261.

Prentice, A. 1996. Constituents of human milk. Food and Nutrition Bulletin 17, 305-12.

Proom, H. and L.M. Hemmons. 1949. The drying and preservation of bacterial cultures. Microbiology 3, 7-18.

Raoufinia, R., A. Mota, N. Keyhanvar, F. Safari, S. Shamekhi, and J. Abdolalizadeh. 2016. Overview of albumin and its purification methods. Advanced Pharmaceutical Bulletin 6, 495-507.

Reinhardt, T.A., R.E. Sacco, B.J. Nonnecke, and J.D. Lippolis. 2013. Bovine milk proteome: quantitative changes in normal milk exosomes, milk fat globule membranes and whey proteomes resulting from Staphylococcus aureus mastitis. Journal of Proteomics 8C, 141-154, article reference 1 is the author listed in the citation.

Rigourd, V., I.D. Brahimi, S. Smii, C. Gobeaux, H. Razafimahefa, T. Hachem, M. Granier, and R. Serreau. 2016. High osmolality of fortifier human milk adding with vitamin (ADEC). Journal of Pharmacology and Clinical Research 1, 1-4.

Rohrig, C.H., S.S. Choi, and N. Baldwin. 2017. The nutritional role of free sialic acid, a human milk monosaccharide, and its application as a functional food ingredient. Critical Reviews in Food Science and Nutrition 57, 1017-1038.

Rueda, R. 2007. The role of dietary gangliosides on immunity and the prevention of infection. British Journal of Nutrition 98 Supplement 1, 68-73.

Rutala, W.A. and D.J. Weber. 2017 update. Centers for Disease Control and Prevention. Guideline for Disinfection and Sterilization in Healthcare Facilities. 161 pgs.

Ryan, J.M, G.E. Rice, and M.D. Mitchell. 2013. The role of gangliosides in brain development and the potential benefits of perinatal supplementation. Nutrition Research 33, 877-87, Abstract only.

(56)         References Cited

OTHER PUBLICATIONS

Saarela, M., I. Virkajarvi, H. Alakomi, P. Sigvart-Mattila, and J. Matto. 2006. Stability and functionality of freeze-dried probiotic Bifidobacterium cells during storage in juice and milk. International Dairy Journal 16, 1477-1482.

Salcedo, J., M. Gormaz, M.C. Lopez-Mendoza, E. Nogarotto, and D. Silvestre. 2015. Human milk bacteriocidal properties: effect of lyophilization and relation to maternal factors and milk components. Journal of pediatric gastroenterology and nutrition 60, 527-32.

Salimei, E. and F. Fantuz. 2012. Equid milk for human consumption. International Dairy Journal 24, 130-142.

Schanler, R.J. 1995. Suitability of human milk for the low-birthweight infant. Clinical Perinatology 22, 207-22, Abstract only.

Schmid, M., F. Guiheneuf, D.B. Stengel. 2016. Evaluation of food grade solvents for lipid extraction and impact of storage temperature on fatty acid composition of edible seaweeds Laminaria digitate (Phaeophyceae) and Pamaria palmate (Rhodophyta). Food Chemistry, sciencedirect printout is 31 pages long.

Serhan, C.N., S. Krishnamoorthy, A. Recchiuti, and N. Chiang. 2011. Novel anti-inflammatory—pro-resolving mediators and their receptors. Current Topics in Medicinal Chemistry 11, 629-47.

Silvestre, D. 2015. Freeze-drying breast milk retains more of its healthy properties. Journal of pediatric gastroenterology and nutrition. Medicalexpress.com/news.

Singh, I., A.K. Rehni, R. Kalra, G. Joshi, M. Kumar, and H.Y. Aboul-Enein. 2007. Ion exchange resins: drug delivery and therapeutic applications. Journal of Pharmaceutical Science 32, 91-100.

Singh, P., A. Thakur, S. Dogra, G. Pankaj, L.M. Srivastav, and N. Kler. 2017. Comparison of osmolality of human milk after fortification with three different fortifiers. Current Medicine Research and Practice 7, Abstract only.

Smith, L.W. and P.W. Emerson. 1924. Notes on the experimental production of dried breast milk. Boston Medical and Surgical Journal 191, 938-40, Abstract only.

Srinivasan, L., R. Bokiniec, C. King, G. Weaver, and A.D. Edwards. 2004. Increased osmolality of breast milk with therapeutic additives. Archives of Disease in Childhood. Fetal and Neonatal Edition 89, F514-F517.

Stefanov, I., et al.: "A novel procedure for routine milk fat extraction based on dichloromethane", Journal of Food Composition and Analysis, Elsevier Ltd., Belgium, vol. 23, 2010, pp. 852-855.

Stamp, L. 1947. The preservation of bacteria by drying. Microbiology 1, 251-265.

Sun, H., S. Han, R. Cheng, M. Hei, F. Kakulas, and S. K. Lee. 2019. Testing the feasibility and safety of feeding preterm infants fresh mother's own milk in the NICU: a pilot study. Nature, Scientific Reports 9, 1-9.

Suranyi, J., G. Wohlmuth, and G. Szakmary. 1960. Manufacture, quality control and use of freeze-dried human milk. Acta Pediatrica Academiae Scientiarum Hungaricae 1, 131-42, Abstract only.

Svensson, M., C. Duringer, O. Hallgren, A.K. Mossberg, A. Hakansson, S. Linse, and C. Svanborg. 2002. Hamlet—A complex from human milk that induces apoptosis in tumor cells but spares healthy cells. Advances in experimental medicine and biology 503, 125-132, Abstract only.

Swanson, K.W. 2009. Human milk as technology and technologies of human milk: medical imaginings in the early twentieth century United States. WSQ: Women's Studies Quarterly 37, 1 & 2, 20-37.

Tack, J., M. Fried, L.A. Houghton, J. Spicak, and G. Fisher. 2006. Alimentary Pharmacology and Therapeutics 24, 183-205.

Talbot, F.B. 1911. Two methods of obtaining milk for hospital use. Boston Medical and Surgical Journal, 164, 304-6.

Thoene, M., C. Hanson, E. Lyden, L. Dugick, L. Ruybal, and A. Anderson-Berry. 2014. Comparison of the effect of two human milk fortifiers on clinical outcomes in premature infants. Nutrients, 261-75.

Van Herwijnen, M.J., M.I. Zonneveld, S. Goerdayal, E.N. Nolte-'t Hoen, J. Garssen, B. Stahl, A.F. Maarten Altelaar, F. A. Redegeld, and M.H. Wauben. 2016. Comprehensive proteomic analysis of human milk-derived extracellular vesicles unveils a novel functional proteome distinct from other milk components. Molecular and Cellular Proteomics 15, 3412-3423, Abstract only.

Vincenzetti, S., M. Savini, C. Cecchini, D. Micozzi, F.M.Carpi, A. Vita, and P. Polidori. 2011. Effects of lyophilization and use of probiotics on donkey's milk nutritional characteristics. International Journal of Food Engineering 7, 1-14.

Weiss G.A., H. Troxler, G. Klinke, D. Rogler, C. Braegger and M. Hersberger. 2013. High levels of anti-inflammatory and pro-resolving lipid mediators, lipoxins, and resolvins and declining docosahexaenoic acid levels in human milk during the first month of lactation. Lipids in Health and Disease 12, 1-12.

Wierzbicki, A., M.S. Taylor, C.A. Knight, J.D. Madura, J.P. Harrington, and C.S. Sikes. Analysis of Shorthorn Sculpin antifreeze protein stereospecific binding to (2-10) faces of ice. Biophysical Journal 71, 8-18.

Williams, F. 2012. The impressive power of breast milk. Discover Magazine. Jun. 2012, 1-4.

Woo J.G., M.L. Guerrero, F. Guo, L.J. Martin, B.S. Davidson, H. Ortega, G.M. Ruiz-Palacios, and A.L. Morrow. 2012. Human milk adiponectin affects infant weight trajectory during the second year of life. Journal of Pediatric Gastroenterology and Nutrition 54, 532-539, Abstract only.

Yoneme, H., J. Hatakeyama, A. Dano, H. Oida, M. Yoshinari, R. Aijima, J. Murata, T. Watanabe, Y. Oki, and M.A. Kido. 2015. Milk basic protein supplementation enhances fracture healing in mice. Nutrition 31, 399-405.

Young, W.H. and K.R. Sutherland. 1922. The design of a machine to powder milk. B.S. thesis, Massachusetts Institute of Technology.

Yoshimura, T., M. Shimoda, H. Ishikawa, M. Miyaki, K. Matsumoto, Y. Osajima, and I. Hayakawa. 2002. Effect of $CO_2$ flow rate on enzyme inactivation by continuous method with microbubbles of supercritical carbon dioxide. Journal of the Faculty of Agriculture Kyushu University 46, 345-352.

Yu, Y., S. Mishra, X. Song, Y. Lasanajak, K.C. Bradley, M.M. Tappert, G.M. Air, D.A. Steinhauer, S. Halder, S. Cotmore, P. Tattersall, M. Agbandje-McKenna, R.D. Cummings, and D.F. Smith. 2012. Functional glycomic analysis of human milk glycans reveals the presence of virus receptors and embryonic stem cell biomarkers. Journal of Biological Chemistry 287, 44784-99.

International Search Report issued on corresponding PCT Application No. PCT/CA2020/050952 dated Oct. 19, 2020, 5 pages.

International Search Report dated Apr. 29, 2020 (Corresponding International Application No. PCT/CA2020/050235 (WO2020168439)).

Written Opinion dated Apr. 29, 2020 (Corresponding International Application No. PCT/CA2020/050235 (WO2020168439)).

International Search Report dated Oct. 19, 2020 (Corresponding International Application No. PCT/CA2020/050952 (WO 2021/003575)).

Written Opinion dated Oct. 19, 2020 (Corresponding International Application No. PCT/CA2020/050952 (WO 2021/003575)).

Abdel-Salam, B.K. 2014. Modulatory effect of whey proteins in some cytokines involved in wound healing in male diabetic albino rats. Inflammation 37, 1616-1622, Abstract only.

Abrams, S.A., S. Landers, L.M. Noble, and B.B. Poindexter. 2017. Donor human milk for the high-risk infant: preparation, safety, and usage options in the United States. American Academy of Pediatrics, Policy Statement. Pediatrics 139, p. 1-6.

Adamkin, D.H. and J.A. Kerner. 2012. Mother's milk, feeding strategies, and lactoferrin to prevent necrotizing enterocolitis. Journal of parenteral and enteral nutrition 36, 25-29.

Adamkin, D.H. and P.G. Radmacher. 2014. Fortification of human milk in very low birth weight infants (VLBW, 1500 g birth weight). Clinical Perinatology 41, 405-21, Abstract only.

Alsaweed, M., C.T. Lai, P.E. Hartmann, D.T. Geddes, and F. Kakulas. 2016. Human milk miRNAs primarily originate from the mammary gland resulting in unique miRNA profiles of fractionated milk. Nature, Scientific Reports, 1-13.

Al-Shehri, S.S., C.L. Knox, H.G. Liley, D.M. Cowley, J.R. Wright, M.G. Henman, A.K. Hewavitharana, B.G. Charles , P.N. Shaw, E.L. Sweeney, and J.A. Duley. 2015. Breastmilk-saliva interactions boost innate immunity by regulating the oral microbiome in early infancy. Public Library of Science One 10, 1-19.

(56)     References Cited

OTHER PUBLICATIONS

Altomare, A., E. Fasol, M. Colzani, X.M. Paredes Para, M. Ferrari, F. Cilurzo, C. Rumio, L. Cannizzaro, M. Carini, P.G. Righetti, and G. Aldini. 2016. An in depth proteomic analysis based on ProteoMiner, affinity chromatography and nano-HPLC-MS/MS to explain the potential health benefits of bovine colostrum. Journal of pharmaceutical and biomedical analysis 121, 297-306, Abstract/ excerpt only.

Bode. 2018. Human Milk Oligosaccharides in the Prevention of Necrotizing Enterocolitis: A Journey From in vitro and in viv Models to Mother-Infant Cohort Studies. Frontiers in Pediatrics, vol. 6.

Anderson, J., K. McKinley, J. Onugha, P. Duazo, M. Chernoff, and E.A. Quinn. 2016. Lower levels of human milk adiponectin predict offspring weight for age: a study in a lean population of Filipinos. Maternal and Child Nutrition 12, 790-800, Abstract only.

Andreas, J., M.J. Hyde, C. Gale, J.R.C. Parkinson, S. Jeffries, E. Holmes, and N. Modi. 2014. Effect of Maternal Body Mass Index on Hormones in Breast Milk: A Systematic Review. Public Library of Science 9, 1-25, Abstract only.

Anonymous: "Human milk R&D" May 31, 2023 XP09305853.

Aragon, F., S. Carino, G. Perdigon, A. de Moreno de Leblanc. 2014. The administration of milk fermented by the probiotic Lactobacillus casei CRL 431 exerts an immunomodulatory effect against a breast tumor in a mouse model. Immunobiology 214, 457-64.

Arnold, L.D.W. 1994. Currents in human milk banking. The lactariums of France: part 1. The Lactarium of Docteur Raymond Fourcade in Marmande. Journal of human lactation 10, 125-6.

Asena, L., E.H. Suveren, G. Karabay, and D. Dursun Altenors. 2017. Human breast milk drops promote corneal epithelial wound healing. Current Eye Research 42, 506-12, Abstract only.

Aydn, M.S, Yiğit, E.N., Vatandaşlar, E., Erdoğan, E., and G. Öztürk. 2018. Transfer and Integration of Breast Milk Stem Cells to the Brain of Suckling Pups. Scientific Reports 8, 9 pgs.

Balaban, M.O., A.G. Arreola, M. Marshall, A. Peplow, C.I. Wei, and J. Cornell. 1991. Inactivation of pectinesterase in orange juice by supercritical carbon dioxide. Journal of Food Science 56, 743-746.

Ballard, O. and A.L. Morrow. 2013. Human milk composition: nutrients and bioactive factors. Pediatric Clinics of North America 60, 49-74.

Baynam, J.T., M.A. Moorman, C. Donnellan, V. Cevallos, and J.D. Keenan. 2013. Antibacterial effect of human milk for common causes of paediatric conjunctivitis. British Journal of Opthamology 97, 377-79, Abstract only.

Belitz, H-D., W. Grosch, and p. Schieberle. 2009. Edible fats and oils. Food Chemistry. Springer, Berlin, p. 640-669.

Bertino, E., M. Giribaldi, E.A. Cester, A. Coscia, B.M. Trapani, C. Peila, S. Arslanoglu, G.E. Moro, and L. Cavallarin. 2017. New human milk fortifiers for the preterm infant. Journal of Pediatric and Neonatal Individualized Medicine 6, p. 1-7.

Bharwani, S.K., B.F. Green, J.C. Pezzullo, S.S. Bharwani, and R. Dhanireddy. 2016. Systematic review and meta-analysis of human milk intake and retinopathy of prematurity: a significant update. Journal of Perinatology 36, 913-20.

Bode, L. 2012. Human milk oligosaccharides: every baby needs a sugar mama. Glycobiology 22, 1147-1162, Abstract only.

Bode, L. and E. Jantscher-Krenn. 2012. Structure-function relationships of human milk oligosaccharides. Advances in Nutrition 3, 383-91, pp. 383S to 391S non consecutive #s.

Bode, L., L. Kuhn, H.Y. Kim, L. Hsiao, C. Nissan, M. Sinkala, C. Kinkasa, M. Mwiya, D.M. Thea, and G.M. Aldrovandi. 2012. Human milk oligosaccharide concentration and risk of postnatal transmission of HIV through breastfeeding. American Journal of Clinical Nutrition 96, 831-39.

Bode, L., N. Contractor, D. Barile, N. Pohl, A.R. Prudden, G.J. Boons, Y.S. Jin., and S. Jennewein. 2016. Overcoming the limited availability of human milk oligosaccharides: challenges and opportunities for research and application. Nutrition Reviews 74, 635-44.

Bomfim, Vanessa S. et al.: "Human milk enriched with human milk lyophilisate for feeding very low birth weight preterm infants: A preclinical experimental study focusing on fatty acid profile", Department of Pediatrics, Children's Hospital, Riberiao Preto Medical School, University of Sao Paulo, Brazil, pp. 1-17, Sep. 25, 2018.

Bornstein, J.C. 2012. Serotonin in the gut: what does it do? Frontiers in Neuroscience 6, article 16, 1-2.

Brandao, M.C., A.P. Carmo, M.J. Bell, and V.C. Anjos. 2010. Characterization of milk by infrared spectroscopy. Revista do Instituto de Laticínios 65, 30-33.

Camilleri, M. 2001. Management of irritable bowel syndrome. Gastroenterology 120, 652-668.

Castillo-Courtade, L., S. Han, S. Lee, F.M. Mian, R. Buck, and P. Forsythe. 2015. Attenuation of food allergy symptoms following treatment with human milk oligosaccharides in a mouse model. Allergy 70, 1091-102, Abstract only.

Castro-Albarran, J., B.R. Aquilar-Uscanga, F. Calon, I. St-Amour, J. Solis-Pacheco, L. Saucier, and C. Ratti. 2016. Spray and Freeze Drying of Human Milk on the Retention of Immunoglobulins (IgA, IgG, IgM). Drying Technology 34, 1801-09.

Cavaletto, M., M.G. Giuffrida, and A. Conti. 2008. Milk fat globule membrane components—a proteomic approach. Advances in Experimental Medicine and Biology 606, 129-41, Abstract only.

Cavazos-Garduno, A., J.C. Serrano-Nino, J.R. Solis-Pacheco, J.A. Gutierrez-Padilla, O. Gonzalez-Reynoso, H.S. Garcia, and B.R. Aquilar-Uscanga. 2016. Effect of pasteurization, freeze-drying, and spray drying on the fat globule and lipid profile of human milk. Journal of Food and Nutrition Research 4, 296-302.

Cederlund, A., Y. Kai-Larsen, G. Printz, H. Yoshio, G. Alvelius, H. Lagercrantz, R. Stromberg, H. Jörnvall, G.H. Gudmundsson, and B. Agerberth. 2013. Lactose in human breast milk an inducer of innate immunity with implications for a role in intestinal homeostasis. Public Library of Science 8, 1-12.

Chelack, B.J., P.S. Morley, and D.M. Haines. 1993. Evaluation of methods for dehydration of bovine colostrum for total replacement of normal colostrum in calves. Canadian Veterinary Journal 34, 407-12.

Choi, A., G. Fusch, N. Rochow, N. Sheikh, and C. Fusch. 2015. Establishment of micromethods for macronutrient contents analysis in breast milk. Maternal and Child Nutrition 11, 761-72.

Choi, A., G. Fusch, N. Rochow, and C. Fusch. 2016. Target fortification of breast milk: predicting the final osmolality of the feeds. PLOS One, p. 1-12.

Christiansen, S. 2010. Chemical composition and nutrient profile of the low molecular weight fraction of bovine colostrum. M.S. thesis. University of Vermont. 55 pgs.

Cohen Engler, A., A. Hadash, N. Shehadeh, and G. Pillar. 2012. Breastfeeding may improve nocturnal sleep and reduce infantile colic: potential role of breast milk melatonin. European Journal of Pediatrics 171, 729-32, Abstract only.

Cohn, E.J., L.E. Strong, W.L. Hughes, D.J. Milford, J.N. Ashworth, M. Melin, and H.L. Taylor. 1946. Preparation and properties of serum and plasma proteins: a system for the preparation into fractions of protein and lipoprotein components of biological tissues and fluids. Journal of the American Chemical Society 68, 459-475.

Cohn, E.J., F.R.N. Gurd, D.N. Surgenor, B.A. Barnes, R.K. Brown, G. Derouaux, J.M. Gillespie, F.W. Kahnt, W.F. Lever, C.H. Liu, D. Mittelman, R.F. Mouton, K. Schmid, and E. Uroma. 1950. A system for the separation of the components of human blood: quantitative procedures for the separation of the protein components of human plasma. Journal of the American Chemical Society 72, 465-474.

Collins, E.B. and B.J. Hall. 1984. Growth of Bifidobacteria in milk and preparation of Bifidobacterium infantis for a dietary adjunct. Journal of Dairy Science 67, 1376-1380.

Cortez, M.V. and E.A. Soria. 2016. The effect of freeze-drying on the nutrient, polyphenol, and oxidant levels of breast milk. Breastfeeding Medicine 11, 551-554, Abstract only.

Craigie, J. 1954. Survival and preservation of tumors in the frozen state. Advances in Cancer Research 2, 197-228, Abstract only.

O'Kennedy, B.T. 2011. Caseins. Chapter 2. In, Handbook of Food Proteins, Woodhead Series in Food Science, Technology and Nutrition, 13-29.

Oftedal, O.T. 2013. Origin and evolution of the major constituents of milk. In: McSweeney P., Fox P. (eds.), Advanced Dairy Chemistry. Springer, Boston, MA. p. 1-42.

(56)                References Cited

OTHER PUBLICATIONS

Patki, S., S. Kadam, V. Chandra, and R. Bhonde. 2010. Human breast milk is a rich source of multipotent mesenchymal stem cells. Human Cell 23, 35-40.

Patki, S., U. Patki, R. Patil, S. Indumathi, P. Kaingade, A. Bulbule, A. Nikam, and A. Pishte. 2012. Comparison of the levels of the growth factors in umbilical cord serum and human milk and its clinical significance. Cytokine 59, 305-8.

Pearson, F., M.J. Johnson, A.A. Leaf. 2013. Milk osmolality: does it matter? Archives of disease in childhood—Fetal and neonatal edition, 98, 166-69.

Perrin, M.T., J. Festival, J., S. Starks, L. Mondeaux, E.A. Brownell, and A. Vickers. 2019. Accuracy and reliability of infrared analyzers for measuring human milk macronutrients in a milk bank setting. Current Developments in Nutrition 3, 7 pgs.

Ryan, J.M, G.E. Rice, and M.D. Mitchell. 2013. The role of gangliosides in brain development and the potential benefits of perinatal supplementation. Nutrition Research 33, 877-87.

Sauret, A., M.C. Andro-Garcon, J. Chauvel, A. Ligneul, P. Dupas, C. Fressange-Mazda, P. Le Ruyet, and A. Dabadie. Osmolality of a fortified human preterm milk: the effect of fortifier dosage, gestational age, lactation stage, and hospital practices. Archives de Pediatrie 25, 411-15.

Schanler, R.J. 1995. Suitability of human milk for the low-birthweight infant. Clinical Perinatology 22, 207-22.

Singh, P., A. Thakur, S. Dogra, G. Pankaj, L.M. Srivastav, and N. Kler. 2017. Comparison of osmolality of human milk after fortification with three different fortifiers. Current Medicine Research and Practice 7.

Smith, L.W. and P.W. Emerson. 1924. Notes on the experimental production of dried breast milk. Boston Medical and Surgical Journal 191, 938-40.

Suranyi, J., G. Wohlmuth, and G. Szakmary. 1960. Manufacture, quality control and use of freeze-dried human milk. Acta Pediatrica Academiae Scientiarum Hungaricae 1, 131-42.

Van Herwijnen, M.J., M.I. Zonneveld, S. Goerdayal, E.N. Nolte-'t Hoen, J. Garssen, B. Stahl, A.F. Maarten Altelaar, F. A. Redegeld, and M.H. Wauben. 2016. Comprehensive proteomic analysis of human milk-derived extracellular vesicles unveils a novel functional proteome distinct from other milk components. Molecular and Cellular Proteomics 15, 3412-3423.

Van Wettere, W.H.E.J., N.L. Willson, S.J. Pain, and R.E.A. Forder. 2016. Effect of oral polyamine supplementation pre-weaning on piglet growth and intestinal characteristics. Animal Journal. Oct 1, 1-5.

Wang, B., P. McVeagh, P. Petocz, and J. Brand-Miller. 2003. Brain ganglioside and glycoprotein sialic acid in breastfed compared with formula-fed infants. American Journal of Clinical Nutrition. 78, 1024-29.

Woo J.G., M.L. Guerrero, F. Guo, L.J. Martin, B.S. Davidson, H. Ortega, G.M. Ruiz-Palacios, and A.L. Morrow. 2012. Human milk adiponectin affects infant weight trajectory during the second year of life. Journal of Pediatric Gastroenterology and Nutrition 54, 532-539.

Yuen, B.H. 1988. Prolactin in human milk: The influence of nursing and the duration of postpartum lactation. American Journal of Obstetrics and Gynecology 158, 583-6.

Hartel, R.W. 2021, Crystallization in Foods. Springer. Ch. 15. pp. 460-478.

Koch, L.E. 2017. Discover the power of horsemilk. (www.powerofhorsemilk.com) Netherlands. (Extract from Website 5pgs).

McHugh, M. and V. Krukonis. 2013. Supercritical fluid extraction: Principles and practice. 2nd edition. Butterworth-Heinemann. pp. 1-16.

Svensson, M., C. Duringer, O. Hallgren, A.K. Mossberg, A. Hakansson, S. Linse, and C. Svanborg. 2002. Hamlet—A complex from human milk that induces apoptosis in tumor cells but spares healthy cells. Advances in experimental medicine and biology 503, 125-131.

Abdel-Salam, B.K. 2014. Modulatory effect of whey proteins in some cytokines involved in wound healing in male diabetic albino rats. Inflammation 37, 1616-1622.

Adamkin, D.H. and P.G. Radmacher. 2014. Fortification of human milk in very low birth weight infants (VLBW, 1500 g birth weight). Clinical Perinatology 41, 405-21.

Altomare, A., E. Fasol, M. Colzani, X.M. Paredes Para, M. Ferrari, F. Cilurzo, C. Rumio, L. Cannizzaro, M. Carini, P.G. Righetti, and G. Aldini. 2016. An in depth proteomic analysis based on ProteoMiner, affinity chromatography and nano-HPLC-MS/MS to explain the potential health benefits of bovine colostrum. Journal of pharmaceutical and biomedical analysis 121, 297-306.

Anderson, J., K. McKinley, J. Onugha, P. Duazo, M. Chernoff, and E.A. Quinn. 2016. Lower levels of human milk adiponectin predict offspring weight for age: a study in a lean population of Filipinos. Maternal and Child Nutrition 12, 790-800.

Andreas, J., M.J. Hyde, C. Gale, J.R.C. Parkinson, S. Jeffries, E. Holmes, and N. Modi. 2014. Effect of Maternal Body Mass Index on Hormones in Breast Milk: A Systematic Review. Public Library of Science 9, 1-25.

Asena, L., E.H. Suveren, G. Karabay, and D. Dursun Altenors. 2017. Human breast milk drops promote corneal epithelial wound healing. Current Eye Research 42, 506-12.

Baynam, J.T., M.A. Moorman, C. Donnellan, V. Cevallos, and J.D. Keenan. 2013. Antibacterial effect of human milk for common causes of paediatric conjunctivitis. British Journal of Opthamology 97, 377-79.

Bode, L. 2012. Human milk oligosaccharides: every baby needs a sugar mama. Glycobiology 22, 1147-1162.

Castillo-Courtade, L., S. Han, S. Lee, F.M. Mian, R. Buck, and P. Forsythe. 2015. Attenuation of food allergy symptoms following treatment with human milk oligosaccharides in a mouse model. Allergy 70, 1091-102.

Cavaletto, M., M.G. Giuffrida, and A. Conti. 2008. Milk fat globule membrane components—a proteomic approach. Advances in Experimental Medicine and Biology 606, 129-41.

Cohen Engler, A., A. Hadash, N. Shehadeh, and G. Pillar. 2012. Breastfeeding may improve nocturnal sleep and reduce infantile colic: potential role of breast milk melatonin. European Journal of Pediatrics 171, 729-32.

Cortez, M.V. and E.A. Soria. 2016. The effect of freeze-drying on the nutrient, polyphenol, and oxidant levels of breast milk. Breastfeeding Medicine 11, 551-554.

Craigie, J. 1954. Survival and preservation of tumors in the frozen state. Advances in Cancer Research 2, 197-228.

El-Shafei, M.M., N.S. Al-Amoudy, and A.K. Said. 1988 a. Effect of the drying process on the nutritive value of milk. Part 1. Biochemical composition. Die Nahrung Molecular Journal of Nutrition 32, 553-57.

El-Shafei, M.M., N.S. Al-Amoudy, and A.K. Said. 1988 b. Effect of the drying process on the nutritive value of milk. Part 2. Biological evaluation. Die Nahrung Molecular Journal of Nutrition 32, 559-64.

Erkmen, O. 1997. Antimicrobial effect of pressurized $CO_2$ on *Staphylococcus aureus* in broth and milk. Journal of Food Science and Technology 71, 826-829.

Farahani, L.A., M. Ghobadzadeh, and P. Yousefi. 2013. Comparison of the effect of human milk and topical hydrocortisone 1% on diaper dermatitis. Pediatric Dermatology 30, 725-729.

Feskanich, D., H.E. Meyer, T.T. Fung, H.A. Bischoff-Ferrari et al., and W.C. Willett. Milk and other dairy foods and risk of hip fractures: a prospective study among postmenopausal women. 2018. Osteoporosis International 29, 385-396.

Friel, J.K., A. Tsopmo, B. Diehl-Jones, and R. Aluko. 2008. Antioxidant properties of human milk fractions. The FASEB Journal 22, 446. (Abstract Only).

Goldman, A.S. 1993. The immune system of human milk: antimicrobial, antiinflammatory and immunomodulating properties. The Pediatric Infectious Disease Journal 12, 664-71.

Gomez-Gallego, C., M.C. Collado, G. Perez, T. Ilo, U.M. Jaakkola, M.J. Bernal, M. J. Periago, R. Frias, G. Ros, and S. Salminen. 2013. Resembling breast milk: influence of polyamine-supplemented formula on neonatal BALB/cOlaHsd mouse microbiota. British Journal of Nutrition 111, 1050-58.

(56)　　　　References Cited

OTHER PUBLICATIONS

Gopinath, B., V.M. Flood, J.C. Louie, J.J. Wang, G. Burlutsky, E. Rochtchina, and P. Mitchell. 2014. Consumption of dairy products and the 15-year incidence of related macular degeneration. British Journal of Nutrition 111, 1673-79.

Gozen, D., S. Caglar, S. Bayraktar, and F. Atici. 2014. Diaper dermatitis care of newborns human breast milk or barrier cream. Journal of Clinical Nursing 23, 515-23.

Greaves, R.I.N. 1960. Preservation of living cells by freeze-drying. Annals of the New York Academy of Sciences 13, 723-8.

Gurnida, D.A., A.M. Rowan, P. Idjradinata, D. Muchtadi, and N. Sekarwana. 2012. Association of complex lipids containing gangliosides with cognitive development of 6-month-old infants. Early Human Development 88, 595-601.

Gutierrez, D. and J.A.G. de Almeida. 1998. Currents in human milk banking: human milk banks in Brazil. Journal of Human Lactation 14, 333-5.

Hahn-Holbrook, T.B. Le, A. Chung, E.P. Davis, and L.M. Glynn. 2016. Cortisol in human milk predicts child BMI (body mass index). Obesity 24, 2471-2474.

Hassiotou, F., D.T. Geddes, and P.E. Hartmann. 2013. Cells in human milk: state of the science. Journal of Human Lactation 29, 171-82.

Hassiotou, F., A. Mobley, D. Geddes, P. Hartmann, and T. Wilkie. 2015. Breastmilk imparts mother's stem cells to the infant. FASEB Journal 29, 876. (Abstract Only).

Heckly, R.J. 1985. Principles of preserving bacteria by freeze-drying. Developments in Industrial Microbiology 26, 379-395.

Human Milk Banking Association of North America (HMBANA). Jun. 2017. Milk Bank FAQ. www.kellymom.com.

Iskarpatyoti, J., E.A. Morse, R.P. McClung, M. Ikizler, J.D. Wetzel, N. Contractor, and T.S. Dermody. 2012. Serotype specific differences in inhibition of reovirus infectivity by human-milk glycans are determined by viral attachment protein. Virology 433, 489-97.

Iwamori, M., K. Takamizawa, M. Momoeda, Y. Iwamori, and Y Taketani. 2008. Gangliosides in human, cow and goat milk, and their abilities as to neutralization of cholera toxin and botulinum type A neurotoxin. Glycoconjugate Journal 25, 675-83.

Jarvinen, K.M. and H. Suomalainen. 2002. Leucocytes in human milk and lymphocyte subsets in cow's milk-allergic infants. Pediatric Allergy and Immunology 13, 243-54.

Jiang, R. and B. Lonnerdal. 2016. Biological roles of milk osteopontin. Current Opinion in Clinical Nutrition and Metabolic Care 19, 214-9.

Kakulas, F. 2015. Breast milk: a source of stem cells and protective cells for the infant. Infant 11, 187-191.

Khailova, L., K. Dvorak, K.M. Arganbright, C.S. Williams, M.D. Halpern, and B. Dvorak. 2009. Changes in hepatic cell junctions structure during experimental necrotizing enterocolitis: effect of EGF treatment. Pediatric Research 66, 140-4.

Kitano, N., K. Tsunoda, T. Tsuji, Y. Osuka, T. Jindo, K. Tanaka, and T. Okura. 2014. Association between difficulty initiating sleep in older adults and the combination of leisure-time physical activity and consumption of milk and milk products: a cross-sectional study. Biomed Central (BMC) Geriatrics 14, 118-25.

Koo, W. and H. Tice. 2018. Human milk fortifiers do not meet the current recommendation for nutrients in very low birth weight infants. Journal of Parenteral and Enteral Nutrition 42, 813-820.

Kunz, C., S. Rudloff, W. Baier, N. Klein, and S. Strobel. 2000. Oligosaccharides in human milk: structural, functional, and metabolic aspects. Annual Review of Nutrition 20, 699-722.

Larque, E., M. Sabater-Molina, and S. Zamora. 2007. Biological significance of dietary polyamines. Nutrition 23, 87-95.

Lin A.E., C.A. Autran, S.D. Española, L. Bode, and V. Nizet. 2014. Human milk oligosaccharides protect bladder epithelial cells against uropathogenic *Escherichia coli* invasion and cytotoxicity. The Journal of Infectious Diseases 209, 389-98.

Lin A.E., C.A. Autran, A. Szyszka, T. Escajadillo, M. Huang, K. Godula, A.R. Prudden, G. Boons, A.L. Lewis, K.S. Doran, V. Nizet, and L. Bode. 2017. Human milk oligosaccharides inhibit growth of group B *Streptococcus*. Journal of Biological Chemistry 292, 11243-49.

Lozano, B., A.I. Castellote, R. Montes, and M.C. Lopez-Sabater. 2014. Vitamins, fatty acids, and antioxidant capacity stability during storage of freeze-dried human milk. International Journal of Food Science and Nutrition 65, 703-7.

Lucas, A., P.J. Lucas, S.I. Chavin, R.L. Lyster, and J.D. Baum. 1980. A human milk formula. Early Human Development 4, 15-21.

McJarrow, P., N. Schnell, J. Jumpsen, and T. Clandinin. 2009. Influence of dietary gangliosides on neonatal brain development. Nutrition Reviews 67, 451-63.

Minami, J., T. Odamaki, N. Hashikura, F. Abe, and J.Z. Xiao. 2016. Lysozyme in breast milk is a selection factor for bifidobacterial colonisation in the infant intestine. Beneficial Microbes 7, 53-60.

Morrow, A.L., G.M. Ruiz-Palacios, M. Altaye, X. Jiang, M.L. Guerrero, J.K. Meinzen-Derr, T. Farkas, P. Chaturvedi, L. K. Pickering, and D.S. Newburg. 2004. Human milk oligosaccharides are associated with protection against diarrhea in breast-fed infants. Journal of Pediatrics 145, 297-303.

Newburg, D.S. 2013. Glycobiology of human milk. Biochemistry 78, 771-85.

Newmark, L.M. 2017. Milk's bioactive ingredients help wounds heal faster. Splash! Milk Science Update, Feb. 2017.

Office Action dated Nov. 10, 2025 (Corresponding Mexican Patent Application No. MX/a/2022/000424).

Office Action dated Apr. 4, 2025 (Corresponding Canadian Patent Application No. 3,146,184).

Office Action dated Mar. 6, 2025 (Corresponding Australian Patent Application No. 2020225089).

Office Action dated Jul. 14, 2025 (Corresponding Australian Patent Application No. 2020310953).

Office Action dated May 16, 2025 (Corresponding Brazilian Patent Application No. BR112021016587-8).

Office Action dated May 28, 2025 (Corresponding Brazilian Patent Application No. BR112021026747-6).

Office Action dated Jun. 11, 2025 (Corresponding European Patent Application No. 20837000.7).

Extended European Search Report dated Oct. 31, 2022 (Corresponding European Application No. 20758712.2).

Extended European Search Report dated Jun. 12, 2023 (Corresponding Application No. 20837000.7).

* cited by examiner

COMPOSITIONS, PROCESSES OF PRODUCTION, STERILIZATION, AND HEALTH-PROMOTING USES OF LYOPHILIZED MILK

CROSS-REFERENCE TO RELATED APPLICATIONS

This application claims the benefit of priority to U.S. Patent Application Ser. No. 62/872,056 entitled "Process of Preparing Lyophilized Milk with Desired Nutritional and Cellular Content" filed Jul. 9, 2019, and U.S. Patent Application Ser. No. 62/873,099 entitled "Novel Uses of Lyophilized Milk" filed Jul. 11, 2019.

FIELD OF INVENTION

The present invention pertains to the field of lyophilization of mammalian milk. In particular novel compositions of lyophilized milk, pharmaceutical or nutraceutical uses of lyophilized milk product in dosage form, and a novel process for preserving and sterilizing mammalian milk, including human milk, as a lyophilized (freeze-dried) product.

BACKGROUND

The composition of human milk is the biological norm for infant nutrition. Human milk also contains many hundreds to thousands of distinct bioactive molecules that protect against infection and inflammation and contribute to immune maturation, organ development, and healthy microbial colonization. Some of these molecules, e.g., lactoferrin, are being investigated as novel therapeutic agents. A dynamic, bioactive fluid, human milk changes in composition from colostrum to late lactation, and varies within feeds, diurnally, and between mothers. Feeding infants with expressed human milk is increasing. Pasteurized donor milk is commonly provided to high risk infants and some mothers express and freeze their milk at some point in lactation for future infant feedings. Many milk proteins are degraded by heat treatment and freeze-thaw cycles and may not have the same bioactivity after undergoing these treatments (Medo, 2012, Reinhardt et al., 2013; Ballard and Morrow, 2013; Sun et al., 2019).

The potential utility of human milk (breast milk, mother's milk) in dry form for easing the demands on mothers (and other caregivers) in simply feeding their babies has been recognized and evaluated for more than a century in the USA (Talbot 1911; Young and Sutherland, 1922; Smith and Emerson, 1924; as reviewed in Swanson, 2009; see also, Jones, 2003).

The concept of preserving the natural quality and nutritional value via rapid freezing of milk was established during initial studies in this field. Similarly, the ability to adjust the relative amounts of milk components during reconstitution of dry milk in water was contemplated.

Freeze-drying as a method of preserving milk has become an accepted practice for certain market sectors. For example, in Europe, freeze-dried human milk is offered to mothers and hospitals on a scale of over 12,000 processed-liters per year through milk banks (Arnold, 1994; Lamireau, 2015: Koettnitz, 2018). More recently, lyophilization of human milk as a preservation method has been evaluated at the first human milk bank in Japan (Mizuno, 2019).

Moreover, lyophilization for preservation and concentration of protein and other fractions from human milk for use in supplementing the supply of milk for babies is well known and has been practiced for decades (Lucas et al., 1980; Hylmo et al., 1984). For example, critical isolates of freeze-dried human milk could be provided as supplements to whole, human milk (de Souza Grance et al., 2015) in feeding preterm infants of very low birth weight in hospitals. Here, costs aside, the paramount considerations are the survival and developing health of the baby.

In Brazil, whole human liquid milk is being enriched with lyophilized whole human milk in hospitals to provide a "fortified" milk for babies that require enhanced nutrition (Bomfin et al. 2018; Oliveira et al. 2019). Premature, low-birth-weight neonates in particular need this extra source for optimal growth and development in their first months.

As discussed above, uses of dried and lyophilized human milk have been focused on supplementing or fortifying milk formulas or pasteurized whole milk for infants.

However, there remains a need for a convenient dosage form of lyophilized/dry mammalian/human milk that can be used as a pharmaceutical or nutraceutical composition without reconstitution or dilution in liquid, for promoting general mammalian/human health.

U.S. Pat. No. 3,297,455 (R. P. Ogden, 1967) discloses a method of freeze drying milk products, which, involves first dehydrating the whole milk using vacuum distillation to reduce up to one-half of the volume, followed by "flash" freezing of the concentrate to form a thin film, which is immediately fragmented into flakes/chips. The resulting frozen flakes/chips are then compacted into a cake/block, which is then dried under a strong vacuum, typically less than 1 mm of Hg, at a temperature that would not lead to melting of the frozen cakes/block.

In addition, there has been particular emphasis in isolation and preservation of specific beneficial components, such as oligosaccharides and certain proteins and peptides, for use in supplementing or fortifying milk formulas or pasteurized whole milk. The fortified products are typically supplied in liquid form for feeding infants, in particular at-risk, premature infants at neonatal, intensive-care units of hospitals.

U.S. Pat. No. 8,361,511 to Hill et al. (2013); U.S. Pat. No. 8,927,027 to Fournell et al. (2015); and 9,539,269 to Chow et al. (2017) disclose such processes. PCT Publication No. WO 2012/030764 (2012) discloses a process for preparing sterile human milk protein compositions, and focused on biochemical fractions of processed human milk with lyophilization as a finishing step.

In other cases, inventors have taught away from use of freeze-drying in processing milk. For example, Sugawara et al. in US Publication No. 2009/0017176 saw no particular advantage to freeze-drying of milk fractions in their process of producing concentrated milk or milk powder, which involves removing ions from milk, and reducing the dissolved oxygen concentration in the milk, followed by subjecting the milk to a heat treatment. Similarly, Kuklinski et al. (US Publication No. 2011/0305764) tried freeze-drying of their preparations but preferred other methods of drying milk, as had been recommended by other workers early on (Friend et al., 1983 a; O'Connor et al., 1986; Chelack et al., 1993). Medo et al. (U.S. Pat. No. 9,149,052) also preferred to exclude lyophilization as a method in preparation of human milk fortifiers.

CN 101422240 (Laigao and Zilei) discloses a production technology for preparation of freeze-dried powder of breast milk (including colostrum) of human body, comprising first concentrating and heat sterilizing the milk followed by freeze drying as a final step. This material was then lyophilized to produce a dry form that could be used in feeding babies.

CN 101530129 (B. Zhang (2012) claimed methodology for production of generic milk powder that would avoid the loss of nutrition and beneficial components as occurs during conventional spray-drying. A freeze-drying step was included at the end of a process that involved a concentration step via vacuum evaporation plus a sterilization step via centrifugation, possibly supplemented with irradiation. Again, supplementation of the powder with beneficial additives was contemplated.

Similarly, Chinese inventor M. Zhang (2013, CN 10249031) taught freeze-drying of donkey's milk after first concentrating the milk via vacuum evaporation followed by heat sterilization.

In addition to preservation, sterilization of milk is also important. Liquid milk for large markets of necessity is pasteurized via heat treatment for specific intervals of time. For example the Holder protocol (lower-temperature, longer-time, LTLT, 63° C. for 30 minutes) or the high-temperature, short-time protocol (HTST: 72° for 15 seconds), mostly sterilizes milk. Pasteurization is believed to lower the numbers of viable microbes enough so that the milk, if kept refrigerated, remains sufficiently fresh for consumption for days or a week or more. The downside of pasteurization is the partial loss of heat-labile, beneficial constituents of the milk. The conditions of pasteurization are set to minimize these losses, but they do occur and can be substantial depending on the specific components of the milk.

Another consideration during lyophilization of whole milk is the make-up of the microbial population thereof. Especially if some pathogenic microbes or viruses occur to some extent in the milk, suppression or elimination of these components is desirable.

It is also believed that pasteurization or otherwise sterilization of lyophilized fresh milk is not necessary, as it is already safely preserved and can be reconstituted as equivalent to fresh milk. However, complete or nearly complete sterilization of lyophilized milk without loss of beneficial components is desired to achieve improved benefits.

Therefore there remains a need for a preservation process which is uncomplicated, easy to be conducted at commercial scale and capable of producing lyophilizing milk with desired nutritional and molecular content but without harmful cellular content.

SUMMARY OF THE INVENTION

An object of the present invention is to provide novel compositions of lyophilized milk, a process for production and sterilization of lyophilized milk, and health-promoting uses of lyophilized milk.

In accordance with another object of the present invention, there is provided an oral dosage form comprising lyophilized mammalian (human) milk and optionally a physiologically acceptable excipient or carrier. The dosage form dosage can be in the from a capsule/caplet, a pill, a tablet, a lozenge, and an oral dissolving strip, and comprises from 1 mg to about 500 mg of the lyophilized dry milk.

In accordance with another object of the present invention, there is provided use of the dosage form described herein as a pharmaceutical or a nutraceutical for improvement of mammalian (human) health.

In accordance with another object of the present invention, there is provided a method of improving health of a mammal comprising administering an oral dosage form comprising a lyophilized mammalian (human) milk and a physiologically acceptable excipient or carrier to a mammal in need thereof.

In accordance with another object of the present invention, there is provided a process for preparing lyophilized mammalian milk with desired nutritional and cellular content. The process comprises a) initially freezing raw milk obtained from a mammalian source; b) cold thawing the initially frozen milk to obtain a flowable concentrate and freezing the flowable concentrate at a temperature from −4° C. to −80° C., at a cooling rate to obtain a layer of predefined thickness, or cryoshaving the frozen milk to obtain frozen flakes/chips and forming a layer of a predefined thickness from said flakes/chips and cooling the formed layer to a temperature from −4° C. to −80° C.; and c) drying the formed layer at a temperature from −20° C. to +60° C. at a pressure from 5 micron Hg to atmospheric pressure to provide the lyophilized human milk.

The process can further comprise treating lyophilized milk via flash supercritical $CO_2$ treatment comprising soaking said lyophilized milk with supercritical $CO_2$ to sterilize the lyophilized milk and/or to reduce harmful cellular content in the lyophilized milk.

DETAILED DESCRIPTION OF THE INVENTION

Unless defined otherwise, all technical and scientific terms used herein have the same meaning as commonly understood by one of ordinary skill in the art to which this invention belongs.

As used herein, the term "about" refers to approximately a +/−10% variation from a given value. It is to be understood that such a variation is always included in any given value provided herein, whether or not it is specifically referred to.

The terms "freeze dried" and "lyophilized" have been used interchangeably in the present application, which mean a substance dried via a low temperature dehydration process that involves freezing the product, lowering the pressure, then removing the ice by sublimation.

The present invention provides lyophilized mammalian (human) milk in a dosage form as a health promoting substance, and use of the lyophilized milk as a pharmaceutical or a nutraceutical for improvement of mammalian (human) health.

The inventor of the present invention has surprisingly found and established that lyophilized human milk can be used in improving general mammalian (human) health by treating and/or ameliorating certain conditions, when the lyophilized milk is formulated in a dosage form, which can be administered locally in the stomach to provide/release a high concentration of the active ingredients of the milk in the stomach, which can provide elevated local dosing that cannot to be achieved by drinking milk in liquid form.

The dosage form can be in the form of a powder, capsule/caplet, a pill, a tablet, a lozenge, and an oral dissolving strip.

The dosage form of the present invention can comprise from 1 mg to 1 g of lyophilized mammalian (preferably human) milk, and optionally a physiologically acceptable excipient or carrier.

In some embodiments, the dosage form comprises about 1 mg to about 500 mg of the lyophilized milk. Preferably, the dosage form comprises about 50 mg to about 200 mg of the lyophilized milk.

The dosage form can be prepared by standard procedures using well-known and readily available ingredients.

In some embodiments, the dosage form can be a dry pressed tablet consisting of 100% lyophilized milk.

In some embodiments, the dosage form of the present invention can be made by mixing the lyophilized dry milk with a physiologically acceptable carrier, or enclosing the lyophilized milk within a carrier.

Non-limiting examples of suitable carriers for the dosage form of the present invention include gelatin, cellulose or its derivatives (such as methylcellulose, sodium carboxymethyl-cellulose hydroxypropylmethylcellulose sense (HPMC), magnesium carbonate, magnesium stearate, sugar, lactose, pectin, dextrin, starch, methylcellulose, cocoa butter, pullulan, modified starches filled carrageenan and/or mixtures thereof and the like.

In some embodiments, a suitable carrier is gelatin, or cellulose or its derivatives.

The capsule of the present invention can be a hard or soft capsule. The capsule shell may contain other additives such as plasticizers, dyes, pigments, opacificant, preservatives, humectants, surfactants, sweetening and/or flavoring agents. The capsule preparation is performed by standard procedures in the pharmaceutical and nutraceutical industry, and can have any shape and size known to those skilled in the art.

Tablets can contain the lyophilized milk in admixture with non-toxic physiologically acceptable excipients or carriers that are suitable for the manufacture of tablets. These excipients may be for example, inert diluents, such as calcium carbonate, sodium carbonate, lactose, calcium phosphate or sodium phosphate: granulating and disintegrating agents for example, corn starch, rice flour, or alginic acid: binding agents, for example starch, gelatin or acacia, and lubricating agents, for example magnesium stearate, stearic acid or talc and other conventional ingredients such as dicalcium phosphate, magnesium aluminum silicate, calcium sulfate, starch, lactose, methylcellulose, and functionally similar materials. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some embodiments, the dosage form is a capsule comprising 100% lyophilized milk encapsulated in gelatin, cellulose or derivatives thereof.

The dosage form can be formulated for quick release, an enteric release, and/or a delayed release.

The dosage form of the present invention can be used as a mammal (preferably human) health promoting substance.

In some embodiments, the dosage form can be used as a pharmaceutical or a nutraceutical for improvement of mammalian (human) health.

In some embodiments, the dosage form comprises lyophilized mammalian milk for improvement of health of a mammal of same genus.

In some embodiments, the dosage form comprises lyophilized human milk for improvement of human health.

The dosage form of the present invention can be useful to promote wound healing, tissue regeneration, bone density promote healthy gut flora, protect against digestive system infection, lessen symptoms of irritable bowel syndrome (IBS), promote intestinal maturation, inhibit harmful microbial growth, protect against antibiotic resistant bacteria, inhibit bladder infections, protect against food allergies, promote sleep, acts as an anti-anxiety agent, necrotizing enteric colitis, antiviral activity, promotes retinal and macular health, to protect against food allergies.

The dosage form of the present invention can be useful in lowering risk: of breast cancer, ovarian cancer, uterine cancer, Alzheimer's disease, osteoporosis, diabetes, cardiovascular disease, stroke later, multiple sclerosis relapses, and in boosting the immune system.

In some embodiments, the improvement of mammalian health is the improvement of digestive health. Non limiting examples of which includes lessening of symptoms of irritable bowel syndrome (IBS), improved tolerance to dairy foods and/or improved regularity. Non limiting example of the irritable bowel syndrome includes inflammatory bowel condition, such as Crohn's disease. Non limiting examples of improved regularity include lessening of diarrhea, lessening of intestinal blockages and/or lessening of constipation.

In some embodiments, the improvement of mammalian health is improvement in immunity, which includes improved wound healing, lessening of symptoms of colds/flu, and/or treatment of skin ailments.

In some embodiments, the improvement of mammalian health includes improvement in sleep quality, weight management, erectile function, and/or mental clarity and outlook.

The dosage form of the present invention can be formulated for administration 1 to 4 times per day.

It has also been found that lyophilized human milk can be incorporated into an acceptable vehicle to form a composition for topical administration to an affected area, such as hydrophobic or hydrophilic creams or lotion. The topical composition comprising lyophilized human milk has been found useful for treating keratinaceous milia. Accordingly, in another embodiment, the present invention provides topical compositions comprising lyophilized mammalian milk and a physiologically acceptable carrier.

In accordance with another aspect, the present invention provides a method of improving health of a mammal (preferably human) comprising administering an oral dosage form to the mammal as described herein.

The method comprises administering the dosage form 1 to 4 times a day. In some embodiments, the method comprises administering the dosage form 1 to 2 times a day.

The beneficial effects on human health obtained by the dosage form of the present invention, as depicted in examples provided herein, are surprising and remarkable as, for example, 100 mg of encapsulated lyophilized milk represents not even 1 milliliter of liquid milk (typically approximately 12% solids as fresh whole milk). However, the method of delivery in a dosage form, such as a capsule, tablet etc., is completely different from the normal mode of delivery—i.e., drinking as a relatively dilute liquid.

Without being bound to a particular mode of action or theory, it appears that the dosage form such as capsule/pill/tablet, landing locally in the stomach, would dissolve and release a concentrate of the actives of human milk, very locally, with a local elevated dosing that would not otherwise be experienced. This in turn might fill binding sites locally or otherwise act to up-regulate beneficial responses in the subject and a specific target organ, which could then result in an amplification and persistence of the desired response.

Such provision of mammalian/human milk, in a dosage form designed to deliver a concentrate on dissolution locally in the body is not found in practice heretofore. In contrast, attempting to "drink" less than 1 ml of milk would scarcely wet the palate. The milk components likely would not even reach the stomach.

The present invention also provides a novel method for preparation of lyophilized mammalian milk, in particular human milk and sterilization thereof.

The processes of the present invention produce lyophilized milk that retains essentially all of its nutritional and health attributes while regulating harmful cellular content.

The process of the present application includes combination of specific steps relating to freezing, storage, shipping, thawing, and the freeze-drying to achieve desired cellular viability.

An additional step, here termed flash supercritical $CO_2$ treatment, is useful for rendering lyophilized milk essentially sterile even if the milk originally has high microbial content, including persistent sub-populations even after freeze-drying.

The process of the present invention comprises an initial freezing step at the site of origin of the milk, wherein the sample is typically stored at approximately –10 to –20° C. for a period prior to shipping, still frozen, to a processing site. At the processing site, the frozen milk is processed to form a thin layer of a predefined thickness at a temperature from –4° C. to –80° C. The formed layer is then lyophilized at a temperature from –20° C. to +60° C. and at a pressure from 5 micron Hg to atmospheric pressure.

In some embodiments, at the processing site, the initially frozen raw milk is cold-thawed slowly under normal refrigeration or at room temperature so that the milk can be poured into a thin enough layer for effective re-freezing and subsequent steps, followed by lyophilization/freeze-drying step. At this stage, the milk is usually first frozen onto a shallow dish or plate within the lyophilizer. Once solidly frozen, the sample is then lyophilized. Re-freezing of the cold thawed raw milk is achieved at a temperature from –4° C. to –80° C., at a cooling rate to obtain a layer of a predefined thickness.

In some embodiments, the initially frozen milk is not thawed to a flowable concentrate at the processing site, but rather is shaved using a cryo-shaving device, or otherwise chipped, for loading still frozen to form thin layers of milk to the lyophilization trays.

In some embodiments, the initial freezing at the site of origin involves slow freezing at about –10° C. to about –30° C.

In some embodiments, the initial freezing at the site of origin involves rapid freezing at about –60° C. to about –80° C.

In some embodiments, the lyophilization step involves slow freezing at about –1 to –10° C. (preferably –4° C.) under and vacuum at about 1 mm Hg.

In some embodiments, the lyophilization step involves rapid freezing at about –60° C. to about –80° C., preferably at about 70° C., under vacuum at about 100-600 microns Hg, preferably at about 200 microns Hg.

In some embodiments, the thickness of the layer formed from the flowable concentrate or the cryoshaved frozen milk is 2 cm or less.

In some embodiments, the layer is formed in a lyophilization dish/plate of a predefined depth.

In some embodiments, the milk layer and lyophilization dish/plate is maintained at a predefined temperature, which is less than the eutectic temperature of ice at the temperature and pressure used in the drying step.

In some embodiments, the sample and lyophilization dish/plate is maintained at a temperature from –20° C. to +60° C., within a lyophilizer having inner wall temperature, cold trap, and/or other surface collecting the sublimated water vapours at about –20° C. or below. In some embodiments, the lyophilization dish/plate is maintained at a temperature about 0° C. to about 50° C. In some embodiments, the lyophilization dish/plate is maintained at a temperature about 25° C. to about 50° C.

In some embodiments, the raw milk is unsterilized, unpasteurized and/or unhomogenized.

In some embodiments, the process further comprises treating the lyophilized milk via flash supercritical $CO_2$ treatment comprising soaking said lyophilized milk with supercritical $CO_2$. In some embodiments, supercritical $CO_2$ is maintained under a pressure from about 2,000 psi to 4,000 psi at a temperature about 40° C. to about 65° C.

The duration of the supercritical $CO_2$ treatment can be from about 30 seconds to about 30 minutes. In some embodiments, the duration of the supercritical $CO_2$ treatment can be from about 30 seconds to about 10 minutes.

In some embodiments, the process also comprises screening the thawed milk for microbial population prior to lyoplilization.

Each parameter of the process of the present invention—freezing temperature, pressure (vacuum) during drying, plate (sample) temperature, thickness (depth) of the frozen sample—is controlled to optimize regulation of harmful microbial cell content in milk, while maintaining the nutritional and beneficial components of the milk. Microbial cell population post-lyophilization is typically substantially reduced. However, sometimes the residual microbial population remains depending on the condition of the original milk and the conditions of lyophilization. The present invention provides a simple, quick, and harmless solution to render residual microbial cell population non-viable in a lyophilized milk via supercritical carbon dioxide treatment of the lyophilized milk as described herein. In addition, the molecular components of milk are preserved in this treatment, which is accomplished at temperatures and times below those required for pasteurization.

In some embodiments, the process of the present application provides a dry material having minimum viability of harmful microbial cell components upon reconstitution of the milk as a liquid.

In some embodiments, the process of the present application provides a dry material having minimum viability of harmful cellular components and maximum nutritional and other health-promoting values upon reconstitution of the milk as a liquid.

In some embodiments, the lyophilized/dry milk including human milk is packaged as powdered samples suitable for reconstitution as a liquid, for example water, for feeding babies, including premature and neonatal infants under care at hospitals and other nursing or wellness centers.

In some embodiments, the lyophilized/dry milk including human milk is packaged as samples for reconstitution as a liquid for feeding babies including premature and neonatal infants under care at hospitals and other nursing or wellness centers in a fortified form by adjusting the amounts of components of milk, for example, proteins or carbohydrates or both, as well as other components.

In some embodiments, the lyophilized/dry milk including human milk obtained from the process of the present application may be supplemented with probiotics, vitamins, minerals, or other health promoting substances for enhanced health and wellness benefits as tabulated and additionally specified herein.

In some embodiments, lyophilized/dry milk including human milk may be prepared as capsules, tablets, pills, lozenges, and other forms for consumption by the general public.

The products made from the lyophilized/dry milk including human milk obtained from the process of the present application can be shown to be safe and free of pathogenic threats, harmful drugs, toxins, and with little or no traces of unwanted common substances such as nicotine and caffeine.

Products made from this process may be provided as capsules, pills, tablets, lozenges, and the like, ready for direct consumption as a health supplement for the general population. The product can also be provided in packets, bottles, jars, and other containers.

As such, upon reconstitution in water or other fluids, the product can also be fed to infants and toddlers as liquid milk. If supplemented nutritional content is necessary or otherwise desired, the make-up formula can be easily adjusted accordingly.

To gain a better understanding of the invention described herein, the following examples are set forth. It will be understood that these examples are intended to describe illustrative embodiments of the invention and are not intended to limit the scope of the invention in any way.

EXAMPLES

Experimental Protocol:
Sourcing, Handling, Analytical, and Safety Screening of Milk:

Freshly expressed human milk was placed in storage bags designed for that purpose and provided to participant mothers by a company that deals in mother's milk. Participants are first assessed through an application process and if approved begin to provide milk. The milk is subjected to safety-screening via a variety of drug and microbial assessments.

The milk was stored at about –10° C. to about –20° C. typically for approximately 1 month at the donor's location, then shipped still-frozen in specialty containers provided for that purpose to the company's storage and analytical facilities.

Local mothers also participated by providing milk that was freshly expressed the same morning that was collected for processing in the studies of the present invention. This milk was not frozen but kept cold prior to the initial processing that same day, and after that it was frozen and otherwise treated as part of the studies.

Prior to processing, the samples of frozen milk were cold-thawed (e.g., at room temperature or less) and sub-samples taken for screening purposes. Microbial populations were measured using microbiological plate kits (3M petri-films) including counts of aerobic bacteria, *E. coli*, total coliforms, enterobacteria, yeast, mold, *Staphylococcus aureus*, and *Listeria* sp.

Nutritive content of the milk was established by measurements of protein, lipids, carbohydrates, total solids, total nonfat solids, osmolality (by freezing point depression) using a FOSS milkoscan. FTIR scans were taken with calibrations based on both human and bovine milks to yield reliable results as compared to standard spectroscopic and other analytical methods (Choi et al., 2015; Fusch et al., 2015). Total solids including total dissolved solids of the original thawed samples and treated samples were measured by standard gravimetric techniques with forced-air drying with comparison of results of weights during and after treatments at 60, 80, 100, and 120° C.
Lyophilization:

Experiments were performed using a lyophilizer from Harvest Right, which is programmable from a digital interface, which also allows data recording to a personal computer or other data logger.

The freezing temperature may range from 0 to –50° C., with rate of cooling also adjustable. The temperature of the sample plate or dish is also programmable from ambient within the instrument to +50° C., with the rate of warming also adjustable. At the same time, the degree of the vacuum within the freeze-drying chamber is also settable, ranging from atmospheric pressure (approximately 760 mm Hg) to an almost complete vacuum of 5 microns of Hg. This is done by adjusting the vacuum valve(s) if desired; one on the vacuum pump, another on the lyophilizer.

Experiments were set up to range from slow freezing at –4° C. and low vacuum, e.g., 1 mm Hg to rapid freezing at –70° C. under high vacuum, e.g., 100 microns Hg. The temperature of the sample plate could be kept at the freezing temperature throughout the process or more typically, it was adjusted upward to a given temperature and vacuum to promote more rapid sublimation of the water. For example, at high vacuum, the plate temperature was set as high as 50° C. Any combinations of these variables within the ranges specified may also be chosen.

Thickness of the milk sample as poured into the sample plate was generally 2 cm or less.

The milk, having been thawed for screening as described, was first weighed into a pyrex dish or dishes. The thickness of the sample was recorded. The dishes were placed on the stainless steel shelves within the sample chamber of the lyophilizer, having been previously brought to the desired temperature, and the door was closed and sealed. The vacuum was not turned on, leaving the pressure at atmospheric.

The sample was monitored visually for freezing, and once frozen—which was verified by opening the chamber and probing the sample with a digital needle thermometer—the time of freezing was recorded. The door closed and sealed, the vacuum was then turned on. When the pressure within the chamber reached the target, the temperature of the plate was raised to its target.

Freeze-drying proceeded with its progress monitored visually. The time was recorded continuously via digital data logging, as were the other process variables. Lyophilization was monitored periodically by turning off the vacuum pump, opening the chamber after venting to atmospheric pressure, removing a dish and weighing it.

This procedure was repeated until the sample reached a constant weight. A subsample at this point was taken, weighed, dried at 60° C. or 80° C. overnight in the forced-air oven, and weighed again. This confirmed the constant weight. In some cases, the sample was then returned to the forced-air oven at 105° C. overnight then reweighed. Any loss in weight pursuant to this procedure was taken as the residual (or bound) water content of the sample.

The sample was then placed into a sealed container along with a small water-vapor scavenging packet (silica gel) to maintain dryness. A subsample was taken for post-processing assessments of the variety of cellular and chemical parameters as described above.

For this part of the protocol, the freeze-dried milk was first reconstituted in water to the value of % total solids as measured in the original thawed sample, in the range of 10 to 14% by weight. The subsequent subsampling and analytical subsample preparations and procedures mirror exactly those that were employed for the original material.

By this protocol, methods, and analytical assessments, the cellular content and variety of biochemical and nutritive parameters before and after freeze-drying of the milk were known.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

Example 1—Freezing of Milk at −10 to −70° C.

Fresh milk samples in 4-ounce collection bags, freshly expressed and kept in transit on ice from the mother's home to the processing lab at 10° C., were prepared by pipetting 15 ml into 20 ml glass vials, previously sterilized by rinsing with 91% isopropanol and drying at 80 to 105° C. The vials were then placed in the upper freezer compartment of a standard home refrigerator or in a commercial upright freezer set at −20° C. The temperature of the compartments was measured using a digital, recording thermometer with a range to −90° C. These small volumes in vials were frozen in 1 to 2 hours at −10 to −20° C.

For rapid freezing at −70° C., an isopropanol (100%) bath containing pellets of dry ice was prepared. The temperature of the bath was recorded at −68 to −72° C. The vials with the milk were partially immersed in the bath. Freezing occurred within 15 minutes.

Freezing experiments of larger volumes of milk were also conducted using small pyrex dishes into which 300 g of human milk were weighed. This milk was provided by participant mothers from a company that deals in human milk, and had previously been stored frozen in 5 gallon pails at −20° C. The milk was cold thawed prior to experiments. The dishes had been sterilized using the isopropanol rinse and heat treatment.

For slower freezing of the milk, the dishes were placed in the upright commercial freezer set at −20° C., with these larger amounts of milk freezing in 5 hours. For rapid freezing, a larger bath of isopropanol plus dry ice was prepared at −68 to −72° C. with up to 3 dishes placed in the bath at a time. Freezing of these occurred within 1 hour.

The frozen samples were kept in the freezers until loaded into the lyophilizer. The pyrex dishes were capped with fitted poly covers, these also previously sterilized with isopropanol followed by heat.

Example 2—Lyophilization of Human Milk Over the Range of Freezing Temperatures (−10 to −70° C.) and Drying Temperatures (Shelf Temperatures) Over the Range of 4° C. to 50° C.

The inner "wall" temperature of the lyophilizer was preset to −20° C. for all experiments, with the shelf temperature typically set to 4, 25, or 50° C. The sublimated water vapor thus freezes on the wall rather than being pulled under vacuum into the pump or otherwise trapped external to the instrument.

In this approach, the instrument was ready-to-receive samples that had been previously frozen at the temperature of a particular experiment. This avoided the overly long freezing time if liquid samples were placed in the instrument for freezing at a particular temperature prior to ramping up the shelf temperature and initiating the vacuum.

In fact, this is the preferred freezing protocol of the present invention rather than having to precool the lyophilizer to a target temperature, which is a time- and energy-consuming step especially at −70° C. Separate commercial instruments and trailers are available for such a freezing step.

Up to 8 dishes of 300 g milk each at a depth of 1.5 cm per dish were placed, 2 each on the 4 shelves of the lyophilizer. Lyophilization to dryness at 4° C. shelf temperature of these samples took up to 48 hours. At 25° C. shelf temperature, the samples were dry in 36 hours. At 50° C. shelf temperature, the samples were dry in 24 hours. Of course, smaller samples with greater surface area and shallower depth dried faster in each case.

The vacuum itself is another variable in the lyophilization process. There are reports that samples dry more slowly if the vacuum is too intense, possibly because the heat exchange is not optimal.

In all of the experiments reported herein, the vacuum was set full-on during the initial evacuation of the lyophilizer. When it reached 200 microns of Hg (200 milliTorr) after about 10 minutes, the pump valve was adjusted to keep the vacuum around that level. It was possible to evacuate the instrument loaded with samples to 10 microns of Hg. For comparison, atmospheric pressure is about 760 millimeters of Hg.

Upon drying and termination of the lyophilization, the dishes were removed, covered, and allowed to warm (or cool, depending on the shelf temperature) to room temperature. The freeze-dried milk at that point was a light, cream color and had formed into friable "sheets" or "tablets" in the curved rectangular form of the dish. When ready, these were chopped by hand with a sterile spatula and poured through a sterile funnel into sterilized sample bottles for later use and analysis.

Example 3—Supercritical $CO_2$ Treatment of Lyophilized Milk

Lyophilization of human milk if performed optimally did inactivate cells as reported herein. However, there frequently remained populations of resistant microbes and other cellular organisms.

Lyophilized, human milk samples were treated with supercritical carbon dioxide using a lab instrument (OCO Labs, SuperC Extractor). The reactor of the instrument is a stainless steel cylinder (4 cm×150 cm) of 100 cubic centimeters internal volume. The operating limits of the instrument are recommended as temperatures up to 90° C. with pressures in the range of 800 to 4,500 psi.

Sample loadings were in the range of 5 to 15 g as dry material. Cellulose filters were placed on either side of the sample with the reactor in a horizontal position. The inflow filter helped to distribute the $CO_2$ on the inlet side and the end filter helped to prevent loss of the sample upon release of the pressure at the end of a treatment as the carbon dioxide passed through the outflow valve of the reactor.

The dry milk samples were "soaked" as opposed to "extracted" in supercritical $CO_2$. That is, the instrument was not operated in flow-through mode, rather the sample was pressurized in the sealed reactor for limited periods ranging from 1 minute to 30 minutes. Exposure times less than 1 minute (e.g. 30 seconds) were also attempted but more difficult to replicate because of the relatively longer time needed to bring the reactor to the target pressure. At the end of the experiment, the pressure was brought to atmospheric rapidly, typically within 30 seconds.

Confirmation of the molecular components being conserved was shown by the yield post treatment being essentially equal (>99% yield) to the sample loadings, especially for the brief treatments in the range of 1 minute to 5 minutes. In the longer experiments, some of the milk fats were seen to be soaked into the cellulose filters, resulting in somewhat lower dry weights of the products post treatment (yields still >95%). In addition, the macronutrient analysis of the samples before and after treatments were equivalent, again with some lowering of the % fats post-treatment due to the "loss" onto the filters.

The overall results of the lyophilization experiments coupled with the supercritical flash treatments are shown in tables 1 and 2. Note that in some cases, the microbial populations of the lyophilized milk were reduced to zero without the flash treatment. In many other cases, the lyophilized milk had greatly reduced microbial counts, which were reduced to zero upon flash treatment with supercritical $CO_2$. Even when the liquid milk was left out so as to develop a heavy population of microbes and even heavier of yeasts (walled cells), the milk could be likewise rendered sterile, devoid of viable cells, when subjected to the combined treatments of lyophilization and flash supercritical $CO_2$.

TABLE 1

Starting Microbial Loadings[a]

| | Total microbial plate counts | Total yeast plate counts |
|---|---|---|
| Fresh, unfrozen human milk | 60 to 65 thousand (K), 6 samples | none |
| Low microbial loading human milk, stored at −20° C. | 14.7 to 21.5 K, 6 samples | none |
| High microbial, no yeast loading human milk, stored at −20° C. | 95.6 K to TNTC, 6 samples | none |
| Medium microbial, high yeast loading human milk, stored at −20° C. | 51.8 to 80.1 K, 6 samples | TNTC[b] |

[a]Microbial counts were made using 3M ™ Petrifilm kits. Sample loadings were 1 ml each, dilutions are indicated as shown in parentheses for each test. Microbes assessed were 1)total aerobic (1:100), 2)total coliform (1:100), 3)*E. coli* (1:100), 4)rapid yeast and mold (1:10), 5)total Enterobacter (1:100), 6)*Staphylococcus* sp. (1:10), and 7)*Listeria* sp. (+/− test, swab); all samples tested negative
[b]TNTC = too numerous to count

TABLE 2

Human milks treated by freezing, lyophilization, and flash supercritical $CO_2$ exposure

| | Freezing temp ° C. | Lyophilization shelf temp ° C. | Supercritical $CO_2$ conditions: psi, ° C., minutes | Total microbial counts: total yeast |
|---|---|---|---|---|
| Fresh, human milk[a] | −20° C. | NAb | NA | 41 to 45 K: none |
| | −70° C. | NA | NA | 47 to 52 K: none |
| | −20° C. | 4° C. | NA | 15.9 K: none |
| | −20° C. | 50° C. | NA | 13 K: none |
| | −20° C. | 50° C. | NA | 24.9 K: TNTC[c,d] |
| | −70° C. | 50° C. | NA | none: none |
| Low microbial loading human milk | −20° C. | NA | NA | negligible[e]: none |
| | −70° C. | NA | NA | negligible: none |
| | −20° C. | 4° C. | NA | negligible: none |
| | −70° C. | 4° C. | NA | negligible: none |

TABLE 2-continued

Human milks treated by freezing, lyophilization, and flash supercritical $CO_2$ exposure

| | Freezing temp ° C. | Lyophilization shelf temp ° C. | Supercritical $CO_2$ conditions: psi, ° C., minutes | Total microbial counts: total yeast |
|---|---|---|---|---|
| High microbial, no initial yeast human milk | −20° C. | NA | | 95.7 K: none |
| | −70° C. | NA | NA | 18.1 K: none |
| | −20° C. | 4° C. | NA | 56.2 K: none |
| | −70° C. | 4° C. | NA | negligible: none |
| Medium microbial, high initial yeast human milk | −20° C. | NA | NA | 70.4 K: TNTC |
| | −70° C. | NA | NA | 37.8K: TNTC |
| | −70° C. | 25° C. | NA | none, TNTC |
| | −70° C. | 50° C. | NA | none, TNTC |
| | −20° C. | 4° C. | 3000 psi, 60° C., 1 min | negligible: none |
| | −20° C. | 4° C. | 3000 psi, 60° C., 2 min | negligible: none |
| | −20° C. | 4° C. | 3000 psi, 60° C., 5 min | negligible: none |
| | −20° C. | 50° C. | 3000 psi, 60° C., 5 min | negligible: TNTC |
| | −20° C. | 50° C. | 3000 psi, 60° C., 10 min | negligible: TNTC |
| | −20° C. | 50° C. | 3000 psi, 60° C., 12 min | negligible: none |
| | −20° C. | 50° C. | 3000 psi, 60° C., 15 min | negligible: none |
| | −20° C. | 50° C. | 3000 psi, 60° C., 20 min | negligible: none |
| | −20° C. | 50° C. | 3000 psi, 60° C., 30 min | negligible: none |
| | −70° C. | 25° C. | 3000 psi, 60° C., 2 min | negligible: none |
| | −70° C. | 25° C. | 3000 psi, 60° C., 5 min | negligible: none |
| High microbial, high initial yeast[f] | −20° C. | NA | NA | TNTC, TNTC |
| | −20° C. | 25° C. | 2200 psi, 45° C., 2 min | 27.7 K, TNTC |
| | −20° C. | 25° C. | 2200 psi, 45° C., 5 min | 23.7 K, TNTC |
| | −20° C. | 25° C. | 2200 psi, 45° C., 10 min | 24.4 K, TNTC |
| | −20° C. | 25° C. | 2200 psi, 45° C., 20 min | 26.2 K, TNTC |
| | −70° C. | 25° C. | 2200 psi, 45° C., 2 min | negligible, none |
| | −70° C. | 25° C. | 2200 psi, 45° C., 5 min | negligible, none |
| | −70° C. | 25° C. | 2200 psi, 45° C., 10 min | negligible, none |
| | −70° C. | 25° C. | 2200 psi, 45° C., 20 min | negligible, none |

[a]milk contributed by separate individual participants
[b]NA = not applicable
[c]TNTC = too numerous to count
[d]second individual participant
[e]no more than a few hundred plates in total inclusive for all microbes tested
[f]samples thawed and left out for 3 days to develop heavy microbial populations

Examples of Uses of Dosage Form of the Present Invention

Example 4—Treatment of Irritable Bowel Syndrome Including Crohn's Disease

A middle-aged mother in her 40's had suffered with Crohn's disease for over 10 years, the disease exhibiting mainly in the lower gastrointestinal tract. Although many medical treatments were attempted, the woman suffered essentially every day. Her diet was severely restricted, owing to intolerance to most types of food, and her weight was very low at less than 100 pounds.

She was provided with 30-capsule bottles of the lyophilized human milk, encapsulated in size 0 proteinaceous, immediate-release capsules or vegan enteric capsules. Each capsule contained either 100 mg or 200 mg of the 100% lyophilized milk powder, with no other additives.

As soon as one day later after commencing dosing at 1 to 2 capsules per day, she noticed an improvement of her condition. The healing progressed quickly within a few days from seriously inflamed to normal. After one month of taking 1 capsule per day of the immediate-release capsules, diagnostic blood tests and histochemical tissue assessments were performed by her physician. The woman was categorized medically as being in remission, with the blood tests indicating so, having documented levels of inflammation at the lowest recorded in the entire course of her disease.

After several months, she had depleted her supply of the capsules. Within a few days without the daily dosing, she experienced a full blown recurrence of the disease. Her supply of the capsules was replenished and again within a couple of days of resuming treatment, the symptoms were greatly reduced, the disease was under control, and again within a month she was in remission. She was able to eat more normally and gain weight.

Her experiences were similar whether the capsules were immediately released in the stomach or delayed (enteric) released in the small intestine, and whether the capsules contained 100 mg or 200 mg of the lyophilized human milk. In each circumstance, the treatment "worked" and her lower GI distress was remarkably alleviated.

Example 5—Treatment of Irritable Bowel Disease

Similar to example 1, a woman in her 60's had long suffered from lower GI disease exhibiting as Crohn's disease. Again, she had been treated by her physician with various medications with little or no improvement. Her disease had become so serious that she was hospitalized for over 1 month, while various treatments were attempted. Ultimately her colon was removed, but she still suffered from the disease. Later, she was provided with both immediate-release capsules and enteric capsules, each containing 100 mg of the lyophilized human milk. Within a few days at 2 to 4 capsules per day of either type of capsule, her symptoms had subsided and within 1 month her condition was in remission. Her physician had been monitoring her blood work and tissue samples. The medical record showed that the epithelium in her ileum, which is where the disease still resided, had returned to normal. She reported that she never felt better.

Later, when her supply of capsules had run out, the disease returned. Her supply was replenished and again when she resumed treatment, her distress ended within a couple of days and the symptoms were gone.

Example 6—Treatment of Irritable Bowel Disease

A professional gastroenterologist had himself long suffered from irritable bowel disease, again expressed as Crohn's disease. He decided to try treating his condition with the human-milk capsules before introducing them to some of the patients. He started treatment with immediate release capsules but did not experience relief of symptoms. He then switched to enteric capsules and within days felt much better, the results even being described as "spectacular". He requested a supply of capsules of both types so that he could initiate a formal study.

Example 7—Treatment of Irritable Bowel Syndrome

IBS encompasses a set of disorders and symptoms. A young woman in her mid-20's suffered digestive discomfort associated with IBS in the form of continuous diarrhea along with other symptoms. She began treatment with 1 or 2 enteric capsules per day, 100 mg whole lyophilized human milk per capsule, for a month. There was no improvement of the symptoms. She then was provided with the immediate release capsules, again 100 mg per capsule of the lyophilized whole human milk. Within one or two days, the symptoms were greatly alleviated and shortly her digestive regularity became normal.

Immediate-Release Versus Enteric Capsules.

This case draws attention to the location of delivery of the lyophilized human milk. Delivery of liquid milk begins in the mouth and proceeds through the throat and then to the stomach, and following that to the small intestine. As mentioned above, the immediate-released capsules dissolve in the stomach. The dissolution of the enteric capsules is delayed, with delivery of the lyophilized milk targeted to the small intestine.

Without being bound to a particular mechanism underlying the differences in health effects upon use of immediate-release versus enteric capsules, it is likely that the different parts of the digestive tract have different types of molecular, cellular, and tissue-based receptors for components of different types of food (Bornstein, 2012; Nakamura et al., 2013). This would mean that the stomach may detect a particular component or set of components among the thousands of components of milk that the small intestine would not, and vice versa. In the case at hand, the beneficial response would appear to have been elicited in the stomach and communicated to other parts of the digestive tract. Bypassing the stomach by use of enteric capsules so that release of the components occurred in the small intestine did not elicit the beneficial response, perhaps because the initial but necessary molecular event was bypassed.

Example 8—Treatment of Discomfort after Consuming Dairy Products

A woman in her 40's had a long history of digestive discomfort with an inability to process dairy foods, without painful digestive distress, among other symptoms. Her condition was undiagnosed over the years although she had been attended by a number of physicians. Her father likewise had a similar history and the consensus was that the condition fit in general on the continuum of irritable digestive disorders, or perhaps food allergies, but without effective treatments, other than avoiding dairy products and other types of food that led to the discomforts. She also avoided gluten-containing foods.

After a few days of consuming the enteric capsules, 1 to 2 capsules per day, 100 mg lyophilized whole human milk per capsule, she felt noticeably better. At that point, she decided to try some dairy products, especially yogurt. She experienced no unpleasant symptoms and was able to process the yogurt in comfort and continues to do so along with the daily consumption of the capsule(s). She had better results with the enteric capsules as compared to the immediate release capsules.

Example 9—Improved Digestive Regularity and Suppression of Intestinal Blockages Associated with Opioid Pain Management A woman in her mid-60's, a chronic pain patient, undergoes opioid pain management attended by her physician and other personnel at the pain clinic. As is common in the circumstances, there were periodic episodes of difficult intestinal blockages as a side effect of opioid use. Upon taking 1 to 2 capsules of the lyophilized human milk, 100 mg per capsule, her regularity became normal and the occurrences of constipation and more severe blockages ceased. In this subject, the immediate-release capsules had a recurring effect of onset of mild nausea. This subject also has difficulty with digesting lactose. Switching to the enteric capsules led to cessation of this problem while maintaining the beneficial effects of digestive regularity, which has persisted for months with dosing of 1 capsule per day.

Example 10—Immunity Boosting with Respect to Cold or Flu Like Symptoms

A male subject in his late 60's had been frequently afflicted with flu-like and cold symptoms each year. He began routinely consuming 1 dose per day of the lyophilized human-milk capsules, 100 mg each. At his work place in the winter months, a flu-like ailment was infecting many of his coworkers, and he was resigned to catching these symptoms and typically would carry them for 2 weeks or so. Once on the regular dosage regimen, although he did notice the onset of a flu-like illness, it persisted only 1 day and was cleared up within 2 days. His improved immunity against cold and flu has persisted for several years with the routine daily dosing.

Example 11—Wound Healing

An older male subject, an outdoorsman and sometimes body builder, was wounded in a forestry accident, receiving small but bloody lacerations on his arm. He had been taking the lyophilized human-milk capsules as above daily for 2 months. He reported that the wounds were noticeably healing by the next day and within a few days were completely healed, with no other treatments beyond routine antibiotic ointment and bandages. He had not experienced rapid healing of this type before, and had thought that he would attend his physician for treatment of the wounds, which was not necessary in this case. This subject works continuously as a handy man and assists in small construction projects. As such, he frequently experiences minor wounds. The rapid healing of these minor scrapes and cuts has become a routine occurrence, since he had begun consuming the capsules on a regular basis.

Example 12—Promotion of Sleep and Improved Fitness

Several male subjects, ranging from early 40's to early 60's in age had difficulty sleeping over a period of years. Upon consuming the immediate-release capsules daily, 1 to 2 capsules per day, they reported improved sleep within a day or so. With continuous dosing of the capsules, they report 6 to 7 hours of restful sleep each night. In one case, the extra capsule per day, if taken in the morning, resulted in drowsiness in the individual. Taking the capsule in the evening was recommended in this case. One of the individuals also reported noticeably improved fitness and energy, and a loss of over 15 pounds over a period of several months, with no particular increase in exercise to account for the improvement.

Example 13—Treatment of Skin Rashes and Other Mild Skin Disorders

A woman in her 60's treated small, keratin white deposits (keratinaceous milia) around her eyes with a topical skin cream made of 100% coconut oil and lyophilized human milk. The topical cream comprising 10 grams of warmed, melted coconut oil (approximately 2 teaspoons) and 10 grams of pure, lyophilized human milk powder (approximately 4 teaspoons of the powder). The powder mixed readily with the liquid coconut oil at approximately 25 to 30° C. On cooling, the mixture became a white cream that was easily applied to the skin. After gently applying the coconut oil/lyophilized human-milk skin cream gently in small amounts as any skin cream might be used, the unwanted deposits were gone within 1 week. The deposits on her skin around her eyes had been persistent for several years and were resistant to all prior treatments. Persistent growths such as these can occur on a variety areas of the body, typically are nonresponsive to antibiotics, and thus practitioners recommend removal by surgical techniques.

Because the lyophilized human milk is biodegradable, 0.1% by weight of sorbic acid or potassium sorbate was added to the formula to preserve the topical skin cream without interfering with the beneficial effects.

Similarly, a male in his 60's treated occasional recurring skin rashes or eczema-like patches with the skin cream as formulated above. The result was rapid disappearance of the patches, as well as suppression of the itching that would often accompany the condition.

Example 14—Treatment of Erectile Dysfunction

A male in his 60's had long experienced erectile dysfunction. He reported much improved function upon daily consumption of the 100 mg, immediate release capsules. He also began adding a small spoonful, roughly 1 gram, of the lyophilized powder to non-dairy beverages, including fruit juices, on a daily basis. He then reported much improved vigor in general and increased daily aerobic activities. As above, he also reported a beneficial effect on digestive regularity.

Example 15—Mental Clarity

Numerous subjects who consumed the capsules on a daily basis reported improvements in mood and mental outlook. This improved attitude accompanied the other improvements and beneficial effects as reported above.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims

REFERENCES

Arnold, L. D. W. 1994, Currents in human milk banking. The lactariums of France: part 1. The Lactarium of Docteur Raymond Fourcade in Marmande. Journal of human lactation 10, 125-6.

Ballard, O. and A. L. Morrow. 2013. Human milk composition: nutrients and bioactive factors. Pediatric Clinics of North America 60, 49-74.

Bomfin, V. S., A. A. Jordao, Jr., L. G. Alves, F. E. Martinez, and J. S. Camelo, Jr. 2018. Human milk enriched with human milk lyophilisate for feeding very low birth weight preterm infants: a preclinical experimental study focusing on fatty acid profile. PLOS One, September 2018, p. 1-17.

Bornstein, J. C. 2012. Serotonin in the gut: what does it do? Frontiers in Neuroscience 6, article 16, 1-2.

Chelack, B. J., P. S. Morley, and D. M. Haines. 1993. Evaluation of methods for dehydration of bovine colostrum for total replacement of normal colostrum in calves. Canadian Veterinary Journal 34, 407-12.

Chow, J., S. R. Davis, R. Buck, G. O. Duska-McEwen, and H. K. Linke. 2017. Methods for decreasing the incidence of necrotizing enterocolitis in infants, toddlers, or children using human milk oligosaccharides. U.S. Pat. No. 9,539,269.

de Souza Grance, T. R., P. de Oliveira Serafin, D. M. C. Thomaz, and D. B. Palhares. 2015. Homologous human milk supplement for very low birth weight preterm infant feeding. Revista Paulista de Pediatria 33, 28-33.

Fournell, J., S. Eaker, S. Elster, and D. J. Rechtman. 2015. Human milk permeate compositions and methods of making and using same. U.S. Pat. No. 8,927,027.

Friend, B. A., K. M. Shahani, C. A. Long, and L. A. Vaughn, 1983, Evaluation of freeze-drying, pasteurization, high-temperature heating and storage on selected enzymes, B-vitamins, and lipids of mature human milk. Journal of Food Protection 46, 330-334.

Hill, J., C. L. Patterson, and A. S. Lynch. 2013. Tasteless nutritional supplement containing free amino acids. U.S. Pat. No. 8,361,511.

Hylmo, P., S. Polberger, I. Axelsson, I. Jakobsson, and N. Raiha. 1984. Preparation of fat and protein from banked human milk: its use in feeding very-low-birth-weight infants. In, Human Milk Banking, A. F. Williams and J. D. Baum, eds. Vevey/Raven Press. pgs. 55-56.

Jones, F. 2003. History of North American donor milk banking: one hundred years of progress. Journal of Human Lactation 19, 313-18.

Koettnitz, F. 2018. Freeze-drying of breast-milk. Elacta European Lactation Consultants Alliance, February 2018, p. 1-4.

Kuklinski, B., R. Schiefer, G. Markolin, R. Kossler, and N. Fuchs. 2011. Use of a mare's milk concentrate dried on a highly-dispersed, biologically inert matrix. U.S. patent application Ser. No. 13/215,960 (Publication No. 2011/0305764).

Laigao, J. and L. Zilei. 2009. Human milk (containing first milk) freeze-drying powder production technique and products and use thereof. CN patent application 101,422,240.

Lamireau, D. 2015. Lyophilization in the human milk of Marmande. Third international congress of the European milk bank association.

Lucas, A., P. J. Lucas, S. I. Chavin, R. L. Lyster, and J. D. Baum. 1980. A human milk formula. Early Human Development 4, 15-21.

Medo, E. M. 2012. Human milk preparation. International patent application WO 2012/030764.

Medo, E. M., A. Montoya, M. Lee, and D. Rechtman. 2015. Methods of obtaining sterile milk and compositions thereof. U.S. Pat. No. 9,149,052.

Mizuno, K. 2019. Human milk bank and donor milk in Japan. International Society for Research in Human Milk and Lactation, First ISRHML China Workshop, Beijing. Abstract.

Nakamura, E., H. Uneyama and K. Torii. 2013. Gastrointestinal nutrient chemosensing and the gut-brain axis: Significance of glutamate signaling for normal digestion. Journal of Gastroenterology and Hepatology 28 (Suppl. 4): 2-8.

O'Connor, C. J., J. R. Longbottom, and P. Walde. 1986. Inactivation of bile-salt-stimulated human milk esterase: effect of storage and heat. Journal of Pediatric Gastroenterology and Nutrition 5, 630-637.

Ogden, R. P. 1967. Method of freeze drying liquid milk products. U.S. Pat. No. 3,297,455.

Oliveira, M. M., D. C. Aragon, V. S. Bomfin, T. M. B. Trevilato, L. G. Alves, A. R. Heck, F. E. Martinez, and J. S. Camelo. 2019. Development of human milk concentrate with human milk lyophilisate for feeding very low birth weight preterm infants: a preclinical experimental study. PLOS One, February 2019, p. 1-16.

Reinhardt, T. A., R. E. Sacco, B. J. Nonnecke, and J. D. Lippolis. 2013. Bovine milk proteome: quantitative changes in normal milk exosomes, milk fat globule membranes and whey proteomes resulting from Staphylococcus aureus mastitis. Journal of Proteomics 8C, pgs. 141-154.

Smith, L. W. and P. W. Emerson. 1924. Notes on the experimental production of dried breast milk. Boston Medical and Surgical Journal 191, 938-40.

Sugawara, T., M. Shiokawa, A. Nakaoka, Y. Kubota, and Y. Komatsu. 2009. Milk material with good flavor and physico-chemical properties and process of producing the same. U.S. patent application Ser. No. 12/065,396 (Publication No. 2009/0017176).

Sun, H., S. Han, R. Cheng, M. Hei, F. Kakulas, and S. K. Lee. 2019. Testing the feasibility and safety of feeding preterm infants fresh mother's own milk in the NICU: a pilot study. Nature, Scientific Reports 9, 1-9.

Swanson, K. W. 2009. Human milk as technology and technologies of human milk: medical imaginings in the early twentieth century United States. WSQ: Women's Studies Quarterly 37, 1 & 2, 20-37.

Talbot, F. B. 1911. Two methods of obtaining milk for hospital use. Boston Medical and Surgical Journal, 164, 304-6.

Young, W. H. and K. R. Sutherland. 1922. The design of a machine to powder milk. B. S. thesis, Massachusetts Institute of Technology.

Zhang, B. 2012. Production method of freeze-dried milk powder. CN patent 101,530,129. Zhang, M. 2013. Method for producing freeze-dried whole donkey milk powder. CN patent 102,429,031.

The invention claimed is:

1. An oral dosage form comprising commercially sterile lyophilized whole human milk and optionally a physiologically acceptable excipient or carrier for use in the treatment of a digestive system disease or disorder, the treatment of a skin disorder, and/or for increasing immunity in a human, wherein said commercially sterile lyophilized whole human milk is produced by a process comprising:

a) initially freezing raw whole milk;

b) cold thawing the initially frozen milk to obtain a flowable concentrate and freezing the flowable concentrate at a temperature from −4° C. to −80° C., to obtain a layer of predefined thickness, or cryoshaving the frozen milk to obtain frozen flakes/chips and forming a layer of a predefined thickness from said flakes/chips and cooling the layer to a temperature from −4°° C. to −80° C.;

c) drying the formed layer at a temperature from −20° C. to +60° C. at a pressure from 5 micron Hg to atmospheric pressure to provide the lyophilized human milk; and d) treating the lyophilized whole human milk via flash supercritical $CO_2$ treatment, to form the commercially sterile lyophilized whole human milk, wherein the commercially sterile lyophilized whole human milk has 90% or more of its immunoglobulins relative to the amount of immunoglobulins present in whole human milk prior to a sterilization step.

2. The dosage form of claim 1 comprising from 1 mg to 500 mg of the commercially sterile lyophilized whole human milk.

3. The dosage form of claim 1 comprising from 50 to 150 mg of the commercially sterile lyophilized whole human milk.

4. The dosage form of claim 1, wherein the dosage form is selected from a capsule/caplet, a pill, a tablet, a lozenge, and an oral dissolving strip.

5. The dosage form of claim 4, further comprising a protein.

6. The dosage form of claim 4, further comprising cellulose or a cellulosic derivative.

7. The dosage form of claim 4, wherein the dosage form is formulated for quick release.

8. The dosage form of claim 4, wherein the dosage form is formulated for an enteric or delayed release.

9. The dosage form of claim 4, which is a dry pressed tablet or pill consisting of the commercially sterile lyophilized whole human milk.

10. The dosage form of claim 4, which is a capsule comprising commercially sterile lyophilized whole human milk encapsulated in gelatin, cellulose or derivatives thereof.

11. The dosage form of claim 1, wherein the dosage form is for use as a pharmaceutical or a nutraceutical.

12. The dosage form of claim 1, wherein the dosage form is for use-in the treatment of symptoms of irritable bowel syndrome, irritable bowel disease, and/or intolerance to dairy foods.

13. The dosage form of claim 12, wherein the irritable bowel disease is Crohn's disease, and wherein the irritable bowel syndrome is diarrhea.

14. The dosage form of claim 1, wherein the dosage form is for management of digestive regularity, wherein the digestive regularity includes treatment of diarrhea, reduction of intestinal blockages and/or reduction of constipation.

15. The dosage form of claim 1, wherein the dosage form is for use in wound healing, the treatment of symptoms of colds/flue, and/or the treatment of skin rashes.

16. The dosage form of claim 1, wherein the dosage form is formulated for administration 1 to 4 times per day.

17. The dosage form of claim 1, wherein the raw milk used in step a) is unsterilized, unpasteurized and/or unhomogenized.

18. The dosage form of claim 1, wherein the flash supercritical $CO_2$ treatment comprises soaking said lyophilized milk with supercritical $CO_2$.

19. The dosage form of claim 1, wherein the supercritical $CO_2$ is maintained under a pressure from about 2,000 psi to 4,000 psi at a temperature between 40° C. and 65° C.

20. The dosage form of claim 1, wherein the freezing in step a) involves slow freezing at about −10° C. to about −30° C. or rapid freezing at about −60° C. to about −80° C.

21. The dosage form of claim 1, wherein the freezing in step b) involves slow freezing at about −1 to −10° C., under vacuum at about 1 mm Hg.

22. The dosage form of claim 1, wherein the freezing in step b) involves rapid freezing at about −60° C. to about −80° C., preferably at about −70° C., under vacuum at about 100-600 microns Hg, preferably at about 200 microns Hg.

23. The dosage form of claim 1, wherein the thickness of the layer formed in step b) is about 2 cm or less.

24. The dosage form of claim 1, wherein the layer formed in step b) is formed in a lyophilization dish or plate of a predefined depth, wherein the lyophilization dish or plate and the milk layer is maintained at a predefined temperature, which is less than the eutectic temperature of ice at the temperature and pressure used in the drying step.

25. The dosage form of claim 24, wherein the lyophilization dish or plate is maintained at a temperature from −20° C. to +60° C., preferably the lyophilization dish or plate is maintained at a temperature about 25° C. to 50° C.

26. The dosage form of claim 1, further comprising screening the thawed milk for microbial and/or other cellular assessment.

\* \* \* \* \*